US008506928B2

(12) United States Patent
Ferrara et al.

(10) Patent No.: US 8,506,928 B2
(45) Date of Patent: Aug. 13, 2013

(54) METHODS AND COMPOUNDS FOR TARGETING TISSUES

(75) Inventors: Katherine Ferrara, Davis, CA (US); Hua Zhang, Davis, CA (US); Jiro Kusunose, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 1282 days.

(21) Appl. No.: 12/206,569

(22) Filed: Sep. 8, 2008

(65) Prior Publication Data

US 2009/0092548 A1   Apr. 9, 2009

Related U.S. Application Data

(60) Provisional application No. 60/970,923, filed on Sep. 7, 2007.

(51) Int. Cl.
*A61K 51/00* (2006.01)
*A61M 36/14* (2006.01)

(52) U.S. Cl.
USPC ....... 424/1.69; 424/1.11; 424/1.65; 424/1.81; 424/1.85; 424/1.89

(58) Field of Classification Search
USPC .................... 424/1.11, 1.65, 1.69, 1.81, 1.85, 424/1.89, 9.1, 9.2, 9.3, 9.4, 9.5, 9.7, 9.8, 424/400, 450, 489; 514/1, 1.11; 530/300, 530/330
See application file for complete search history.

(56) References Cited

U.S. PATENT DOCUMENTS

| 6,241,964 B1 * | 6/2001 | Burns et al. | 424/1.89 |
| 6,696,081 B2 * | 2/2004 | Grinstaff et al. | 424/450 |
| 2006/0160743 A1 * | 7/2006 | Zhang et al. | 514/15 |

FOREIGN PATENT DOCUMENTS

JP          2000336099      * 12/2000

OTHER PUBLICATIONS

Bao, A. et al., "Direct $^{99m}$Tc Labeling of Pegylated Liposomal Doxorubicin (Doxil) for Pharmacokinetic and Non-Invasive Imaging Studies," The Journal of Pharmacology and Experimental Therapeutics, 2004, pp. 419-425, vol. 308, No. 2.
Bao, A. et al., "$^{186}$Re-Liposome Labeling Using $^{186}$Re-SNS/S Complexes: In Vitro Stability, Imaging, and Biodistribution in Rats," The Journal of Nuclear Medicine, Dec. 2003, pp. 1992-1999, vol. 44, No. 12.
Brissette, R. et al., "Identification of Cancer Targets and Therapeutics Using Phage Display," Current Opinion in Drug Discovery & Development, 2006, pp. 363-369, vol. 9, No. 3.
Ding, B-S. et al., "Advanced Drug Delivery Systems That Target the Vascular Endothelium," Molecular Interventions, Apr. 2006, pp. 98-112, vol. 6, Issue 2.
Gerlag, D.M. et al., "Suppression of Murine Collagen-Induced Arthritis by Targeted Apoptosis of Synovial Neovasculature," Arthritis Res., 2001, pp. 357-361, vol. 3, No. 6.
Hajitou, A. et al., "Vascular Targeting: Recent Advances and Therapeutic Perspectives," Trends in Cardiovascular Medicine, 2006, pp. 80-88, vol. 16, No. 3.
Kamps, J.A.A. et al., "Massive Targeting of Liposomes, Surface-Modified with Anionized Albumins, to Hepatic Endothelial Cells," Proceedings of the National Academy of Sciences of the United States of America, Pharmacology, Oct. 1997, pp. 11681-11685, vol. 94, No. 21.
Koning, G.A., "Targeting of Angiogenic Endothelial Cells at Sites of Inflammation by Dexamethasone Phosphate-Containing RGD Peptide Liposomes Inhibits Experimental Arthritis," Arthritis and Rheumatism, Apr. 2006, pp. 1198-1208, vol. 54, No. 4.
Lestini, B.J. et al., "Surface Modification of Liposomes for Selective Cell Targeting in Cardiovascular Drug Delivery," Journal of Controlled Release, 2002, pp. 235-247, vol. 78, No. 1-3.
Lukyanov, A.N. et al., "Tumor-Targeted Liposomes: Doxorubicin-Loaded Long-Circulating Liposomes Modified with Anti-Cancer Antibody," Journal of Controlled Release, 2004, pp. 135-144, vol. 100, No. 1.
Marik, J. et al., "Long-Circulating Liposomes Radiolabeled with [$^{18}$F]Fluorodipalmitin ([$^{18}$F]FDP)," Nuclear Medicine and Biology, 2007, pp. 165-171, vol. 34, No. 2.
Maruyama, K. et al., "Lipid Composition is Important for Highly Efficient Target Binding and Retention of Immunoliposomes," Proc. Natl. Acad. Sci. USA, Aug. 1990, pp. 5744-5748, vol. 87, No. 15.
Moghimi, S.M. et al., "Methylation of the Phosphate Oxygen Moiety of Phospholipid-Methoxy (Polyethylene Glycol) Conjugate Prevents PEGylated Liposome-Mediated Complement Activation and Anaphylatoxin Production," The FASEB Journal, 2006, pp. 2591-2593, vol. 20, No. 14.
Patel, L.N. et al., "Cell Penetrating Peptides: Intracellular Pathways and Pharmaceutical Perspectives," Pharmaceutical Research, Nov. 2007, vol. 24, No. 11.
Raffaghello, L. et al., "Immunoliposomal Fenretinide: A Novel Antitumoral Drug for Human Neuroblastoma," Cancer Letters, 2003, pp. 151-155, vol. 197, No. 1-2.
Ruoslahti, E., "Vascular Zip Codes in Angiogenesis and Mestastasis," Biochemical Society Transactions, 2004, pp. 397-402, vol. 32, Part 3.
Schiffelers, R.M. et al., "Anti-Tumor Efficacy of Tumor Vasculature-Targeted Liposomal Doxorubicin," Journal of Controlled Release, 2003, pp. 115-122, vol. 91, No. 1-2.
Sen Gupta, A. S. et al., "RGD-Modified Liposomes Targeted to Activated Platelets as a Potential Vascular Drug Delivery System," Thrombosis and Haemostasis, 2005, Prepublished Online Dec. 8, 2004, pp. 106-114, vol. 93, No. 1.
Shadidi, M. et al., "Selective Targeting of Cancer Cells Using Synthetic Peptides," Drug Resistance Updates, 2003, pp. 363-371, vol. 6, No. 6.
Simberg, D. et al., "Biomimetic Amplification of Nanoparticle Homing to Tumors," Proceedings of the National Academy of Sciences of the United States of America, Jan. 16, 2007, pp. 932-936, vol. 104, No. 3.

(Continued)

*Primary Examiner* — D L Jones
(74) *Attorney, Agent, or Firm* — Fenwick & West LLP

(57) ABSTRACT

The present invention relates to peptides which home to cells, e.g. heart cells, with high selectivity and which can be useful in the form of compositions. Such compositions can be used, e.g., for selectively targeting a systemically administered therapeutic agent or imaging agent to a cell or tissue in a subject. The present invention further relates to methods of using the compositions for imaging, e.g. PET imaging, and targeting cells, e.g. for delivering a therapeutic agent to one or more target cells in a subject.

41 Claims, 17 Drawing Sheets

(56) References Cited

OTHER PUBLICATIONS

Sutcliffe-Goulden, J.L., "The Synthesis of Novel $^{18}$F-Labelled Peptides for PET," Doctor of Philosophy Thesis, University of London, Jul. 2002, 278 pages.

Tilcock, C. et al., "$^{99m}$Tc-Labeling of Lipid Vesicles Containing the Lipophilic Chelator PE-DTTA: Effect of Tin-to-Chelate Ratio, Chelate Content and Surface Polymer on Labeling Efficiency and Biodistribution Behavior," Nuclear Medicine and Biology, 1994, pp. 89-96, vol. 21, No. 1.

Torchilin, V.P., "Recent Advances with Liposomes as Pharmaceutical Carriers," Nature Reviews, Drug Discovery, Feb. 2005, pp. 145-160, vol. 4, No. 2.

Van Rooijen, N. et al., "Liposome-Mediated Depletion of Macrophages: Mechanism of Action, Preparation of Liposomes and Applications," Journal of Immunological Methods, 1994, pp. 83-93, vol. 174, No. 1-2.

Wiewrodt, R. et al., "Size-Dependent Intracellular Immunotargeting of Therapeutic Cargoes into Endothelial Cells," Blood, Feb. 1, 2002, pp. 912-922, vol. 99, No. 3.

Wilson, A. et al., "Targeted Delivery of Oligodeoxynucleotides to Mouse Lung Endothelial Cells in Vitro and in Vivo," Molecular Therapy, Sep. 2005, pp. 510-518, vol. 12, No. 3.

Zhang, L. et al., "Molecular Profiling of Heart Endothelial Cells," Circulation, 2005, pp. 1601-1611, vol. 112, No. 11.

\* cited by examiner i j

Labeled with F-18
autoradiography

No surgery

With surgery

SEQUENCE LISTING

```
<160> NUMBER OF SEQ ID NOS: 7

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Cys Arg Pro Pro Arg
1               5

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Cys Pro Pro Arg Arg
1               5

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Cys Arg Arg Arg Arg
1               5

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Cys Ala Arg Pro Ala Arg
1               5

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Cys Pro Lys Arg Pro Arg
1               5
```

```
<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Arg Gly Asp Tyr Lys Glu
1               5

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Cys Arg Arg Pro Pro
1               5
```

METHODS AND COMPOUNDS FOR TARGETING TISSUES

CROSS REFERENCE TO RELATED APPLICATIONS

This application claims the benefit of U.S. Provisional Application No. 60/970,923, filed Sep. 7, 2007, the entire disclosure of which is hereby incorporated by reference in its entirety for all purposes.

STATEMENT REGARDING FEDERALLY SPONSORED RESEARCH OR DEVELOPMENT

The U.S. Government has certain rights in this invention pursuant to Grant Nos. CA103828 and CA R24 110804 awarded by the National Institutes of Health.

SEQUENCE LISTING

The instant application contains a Sequence Listing which has been submitted in ASCII format via EFS-Web and is hereby incorporated by reference in its entirety. Said ASCII copy, created on Sep. 8, 2011, is named 145991CRF_sequencelisting.txt and is 1,688 bytes in size.

BACKGROUND OF THE INVENTION

1. Field of the Invention

The present invention relates generally to the fields of molecular medicine, drug and gene delivery, imaging, and, more specifically, to novel compositions and methods for treating and/or diagnosing diseases such as cardiovascular diseases and brain diseases.

2. Description of the Related Art

The vascular endothelium has been recognized as an important target for therapeutic interventions which use liposomes or other particles to carry drugs and/or genes. See Ding et al., Molecular Interventions 2006; 6(2):98-112.; Hajitou et al., Trends in Cardiovascular Medicine 2006; 16(3):80-88. Specific adhesion to normal or pathological organs has been reported using ligands tailored to vascular zip codes or luminally-expressed pathological targets. See Ruoslahti, Biochem Soc Trans 2004; 32:397-402.; Zhang et al., Circulation 2005; 112(11):1601-1611.; Brissette et al., Curr Opin Drug Discov Dev 2006; 9(3):363-369. Other previous studies have targeted particles to tumor vessels and tumor cells, effectively combining the enhanced permeability and retention effect within tumors with the effect of the targeting ligand. See Ding et al., Molecular Interventions 2006; 6(2):98-112.; Torchilin, Nature Reviews Drug Discovery 2005; 4(2):145-160.

Among various drug-gene delivery particles, targeted phospholipid-based liposomes have been widely studied but have had limited clinical impact. In limited pre-clinical studies, antibody targeting of liposomes to intravascular targets has shown impressive localization of delivery vehicles and subsequent therapeutic effect. See Raffaghello et al., Cancer Lett 2003; 197(1-2):151-155.; Lukyanov et al., Journal of Controlled Release 2004; 100(1):135-144. However, a major drawback of antibody targeted liposomes is low tissue penetration and high molecular weight. In contrast, small peptides and small molecules that selectively recognize cell surface markers can be employed to target vehicles. See Torchilin, Nature Reviews Drug Discovery 2005; 4(2):145-160.; Shadidi et al., Drug Resistance Updates 2003; 6(6):363-371.; Schiffelers et al., Journal of Controlled Release 2003; 91(1-2):115-122.; Lestini et al., Journal of Controlled Release 2002; 78(1-3):235-247.

The short linear peptide CRPPR (SEQ ID NO: 1) has previously been reported to specifically bind to the heart endothelium. See Zhang et al., Circulation 2005; 112(11): 1601-1611. Other short linear arginine-containing peptides were similarly identified by phage display and demonstrated substantial but less specific cardiac targeting. See Zhang et al., Circulation 2005; 112(11):1601-1611. However, it is unclear whether any of these peptides can be used for targeting drug-gene delivery particles to the vasculature or what features may be required to maximize delivery.

Thus a need exists for a composition that can be used to specifically deliver compounds to a cell of interest while also maximizing efficacy, decreasing art known immunogenic effects against the composition, and expanding the potential applications of the composition to other diseases and utilities. The present invention provides for these and other advantages, as described below.

SUMMARY OF THE INVENTION

Disclosed herein are compositions for delivering a compound, e.g., a therapeutic or imaging agent to a cell, and methods for using the compositions. Accordingly one aspect of the invention is a composition for delivering a compound to a cell, the composition having at least one peptide with a free C-terminus and a linked N-terminus and a plurality of amino acid residues, the peptide having a C-terminal arginine residue positioned at the free C-terminus of the peptide, wherein the peptide targets the composition to the cell; the composition also having a particle for carrying the compound and a linking molecule to link the peptide at the linked N-terminus to the particle. The linking molecule is of sufficient length to expose the C-terminal arginine residue positioned at the free C-terminus of the at least one peptide.

In one aspect, the compound delivered by the composition is, e.g., a therapeutic agent or an imaging agent. Examples include but are not limited to amnioterone and digoxin. The compound can include a radiolabel, e.g., [$^{18}$F], [$^{18}$F]FDP, or $^{64}$Cu. In one embodiment, the compound is [$^{18}$F]FDP. The composition can include a dye. In some embodiments, the composition further comprises the compound to be delivered.

A described herein, the composition has a peptide that includes a C-terminal arginine residue positioned at the free C-terminus. In some embodiments, the composition includes a peptide with a plurality of arginine residues at said free C-terminus of said peptide. In other embodiments, the peptide has two arginine residues at said free C-terminus of said peptide. Example peptides include but are not limited to those with amino acid sequences including PPR. In one embodiment, the peptide has a CPPRR amino acid sequence (SEQ ID NO: 2) or a CRRRR amino acid (SEQ ID NO: 3) at the free C-terminus. In one embodiment, the composition of the invention does not include peptides with amino acid sequences: CRPPR (SEQ ID NO: 1), CARPAR (SEQ ID NO: 4), and CPKRPR (SEQ ID NO: 5) at the free C-terminus of said peptide.

In one variation the peptide is a dimeric peptide that is, e.g., covalently dimerized. In some embodiments, the peptide binds a scavenger receptor. The peptide can have a net positive charge at a given pH, e.g., a net positive charge at pH 7.2.

In some embodiments, the peptide is about 2-6 mol percent of the composition of the invention. In one embodiment, the peptide is about 6 mol percent of the composition. The composition can have a plurality of peptides, e.g., at least 6000 peptides or, e.g., at least 6000 dimeric peptides.

The peptide of the composition has 5 or more, 6 or more, 7 or more, 8 or more, 9 or more, 10 or more, 50 or more, 500 or more, or 5000 or more amino acid residues. In one embodiment, the peptide has 5 amino acid residues. In addition, the peptide comprises at least 10 percent, 20 percent, 30 percent, 40 percent, 50 percent, or at least 80 percent arginine residues. In one embodiment the peptide comprises 40 percent arginine residues. The composition can have one or a plurality of peptides. In one embodiment, the composition has at least 6000 peptides or at least 6000 dimeric peptides.

The composition of the invention includes a particle for carrying the compound to be delivered to the cell. In various embodiments the particle is, e.g., a liposome, a phospholipid based liposome, a microbubble, a nanodroplet, a virus, a caveolae, or a micelle. The particle can include at least one fatty acid and/or at least one lipid, e.g., DPPC. The particle can include a phospholipid-based liposome. In some embodiments, the phospholipid-based liposome includes, e.g., a DPPC, an LPP, and/or a DSPE-PEG2000. In one variation the particle includes a brush layer. The brush layer can includes, e.g., PEG and/or DSPE-PEG2000. In one embodiment the brush layer is about 2000 Mw.

The composition of the invention includes a linking molecule linking the peptide to the particle. In one aspect the linking molecule includes PEG. The linking molecule can be about 3600 Mw. In one embodiment linking molecule is of sufficient length to expose the terminal arginine residue of said free C-terminus of said at least one peptide, e.g., of sufficient length to expose said terminal arginine residue of said free C-terminus of said at least one peptide beyond said brush layer.

The composition of the invention is used to deliver a compound to a cell. Cells include, e.g., a mammalian cell, a human cell, a cardiac cell, an endothelial cell, a cardiac endothelial cell, a HCAEC cell, a HUVEC cell, a brain cell, or a cancer cell. In one embodiment the cell is a cardiac endothelial cell. In another embodiment the composition is used for PET imaging.

One aspect of the invention is a composition for delivering a compound to a cell, the composition having a plurality of peptides, wherein said peptides comprise a CPPRR amino acid sequence (SEQ ID NO: 2) or a CRRRR amino acid sequence (SEQ ID NO: 3) at the free C-terminus of said peptides and said peptides are dimerized; a liposome comprising a PEG brush layer of 2000 Mw, wherein said liposome further comprises DPPC and the compound [18F]FDP, and wherein said liposome is coated with 6 mol % of said peptides; and a linking molecule comprising a PEG spacer of 3600 Mw, wherein said linking molecule links said peptides and said liposome.

In addition, the invention provides methods of using the composition described herein for delivery of compounds to cells. For example, the invention provides a method for targeting a compound to a cell by administering the compositions described herein to a subject wherein the composition carries said compound. The compound can be, e.g., a therapeutic agent and/or an imaging agent. In one embodiment the compound is an imaging agent. The cell can be but is not limited to a tumor cell, a cardiac cell, or a brain cell.

In some embodiments administering is performed via injection. The method can include pre-administration of polyinosinic acid, a plurality of particles alone, clodronate liposomes, or a plurality of peptides alone. The method can also include imaging the subject.

The subject can be any in need of treatment or observation, including a human. In some embodiments the method is used to treat a condition in the subject. Conditions include but are not limited to an ischemic condition or a brain condition.

In one aspect the invention provides a method of imaging an imaging agent in a subject using positron emission tomography (PET) by administering a composition having at least one peptide, a particle, a compound, and a linking molecule, and imaging a region of interest (ROI) in the subject using PET. The peptide has a free C-terminus and a linked N-terminus and a plurality of amino acid residues and a C-terminal arginine residue positioned at said free C-terminus, wherein said peptide targets the composition to the cell; the particle is for carrying the compound; and the linking molecule links the at least one peptide at said linked N-terminus to the particle. The linking molecule is of sufficient length to expose the C-terminal arginine residue positioned at said free C-terminus of the at least one peptide.

In one embodiment of the imaging method, the compound includes [$^{18}$F]FDP. Administering can be, e.g., via injection. The subject can be, e.g., human. In one aspect, the imaging method produces an image of the ROI in one minute or less.

In another aspect, the invention provides a method for a release of a compound to a brain in a subject. The method includes administering the composition described herein to the subject, wherein the composition includes the compound; and allowing the compound to metabolize in the subject. In one embodiment administering is performed via injection. In another embodiment the subject is human. The compound is, e.g., amnioterone, digoxin, or a therapeutic agent.

The invention also includes an isolated peptide of five or more amino acid residues with a terminal amino acid sequence selected from the group consisting of CPPRR (SEQ ID NO: 2) and CRRRR (SEQ ID NO: 3), wherein R is located at a free C-terminus of the peptide. In some embodiments the peptide has a net positive charge at pH 7.2. The peptide can be dimerized. The peptide can bind a scavenger receptor.

BRIEF DESCRIPTION OF THE SEVERAL VIEWS OF THE DRAWINGS

These and other features, aspects, and advantages of the present invention will become better understood with regard to the following description, and accompanying drawings, where:

FIG. 4. Well counts (% ID/g) obtained 90 minutes after injection. (a), (b) and (c), with different LPP; (d), with varied ratios of CRPPR-3:DSPE-PEG2000 ('CRPPR' disclosed as SEQ ID NO: 1). Significance of the accumulation of compositions targeted with CRPPR-3:DSPE-PEG2000 ('CRPPR' disclosed as SEQ ID NO: 1) 6%:6% tested against other peptides and surface architectures is shown by *, p<0.001; , p<0.01;*, p<0.05. In 4a with CRPPR-3 ('CRPPR' disclosed as SEQ ID NO: 1), accumulation in each organ is tested against accumulation in the heart. Significance of accumulation is otherwise tested against CRPPR-3 ('CRPPR' disclosed as SEQ ID NO: 1) in the same organ.

FIG. 5A discloses 'CRPPR' as SEQ ID NO: 1, FIG. 5B discloses 'CRPPR' as SEQ ID NO: 1 and 'CRRRR' as SEQ ID NO: 3. FIG. 5C discloses 'CRPPR' as SEQ ID NO: 1 and 'CRRRR' as SEQ ID NO: 3.

FIGS. 6A-B disclose 'CRPPR' as SEQ ID NO: 1.

DETAILED DESCRIPTION OF THE INVENTION

Definitions

Figure 1:
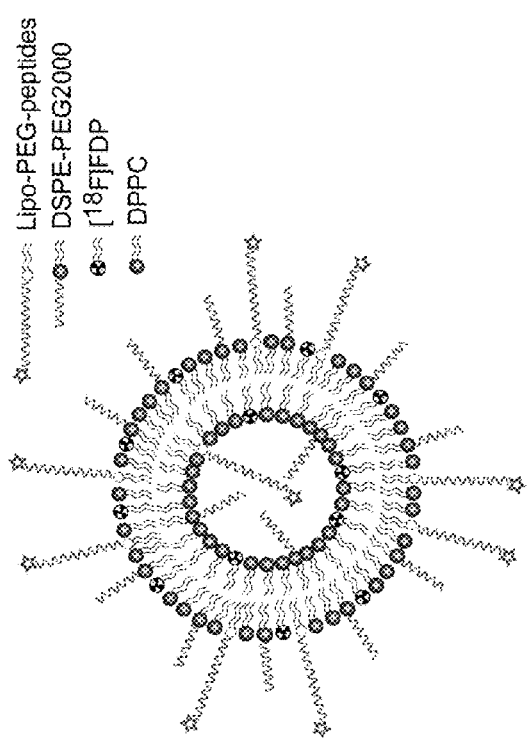
FIG. 1. (a) Chemical structures of lipo-PEG-peptides (LPPs) and (b) schematic of radiolabeled targeted liposome. Molecular weights of the PEG spacer are 1200, 2400, 3600 for m=1, 2, 3, respectively. Abbreviations for the LPPs are as follows. CRPPR-3 ('CRPPR' disclosed as SEQ ID NO: 1): peptide=CRPPR (SEQ ID NO: 1), m=3; CRPPR-2 ('CRPPR' disclosed as SEQ ID NO: 1): peptide=CRPPR (SEQ ID NO: 1), m=2; CRPPR-1 ('CRPPR' disclosed as SEQ ID NO: 1): peptide=CRPPR (SEQ ID NO: 1), m=1; RGD-3: peptide=c (RGDY(OMe)KE) (SEQ ID NO: 6), m=3; CPPRR-3 ('CPPRR' disclosed as SEQ ID NO: 2): peptide=CPPRR (SEQ ID NO: 2), m=3; CRRPP-3 ('CRRPP' disclosed as SEQ ID NO: 7): peptide=CRRPP (SEQ ID NO: 7), m=3; CRRRR-3 ('CRRRR' disclosed as SEQ ID NO: 3): peptide=CRRRR (SEQ ID NO: 3), m=3; NON indicates no LPP (but 12% DSPE-PEG2000); NT indicates in vitro incubation without liposomes. LPPs are incorporated within a liposome prior to injection with a formulation of LPP: DSPE-PEG2000: DPPC=6:6:88 (mol/mol), except in FIG. 4d. (c) Fluorescence intensity, as measured by flow cytometry, for a melanoma cell line, A375, and an endothelial cell line, Human Coronary Artery Endothelial Cells (HCAEC) incubated with liposomes containing CRPPR-3 lipo-PEG-peptides ('CRPPR' disclosed as SEQ ID NO: 1). Fluorescent, viable cells were quantified after incubation and washing.
Figure 1:
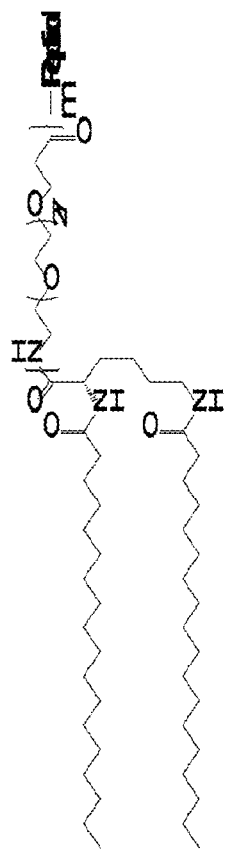

Terms used in the claims and specification are defined as set forth below unless otherwise specified.

The term "DPPC" refers to the phospholipid 1,2-Dipalmitoyl-snglycero-3 phosphocholine. DPPC is useful, e.g., in liposomes.

The term "FDP" refers to fluorescent donor probe. Examples of FDP include [$^{18}$F]FDP.

The term "LPP" refers to lipo-PEG-peptide, typically an LPP composition includes a liposome, a PEG linking molecule, and a peptide.

The term "DSPE-PEG2000" refers to 1,2 distearoyl-sn-glycero-3-phosphoethanolamine-N-[Methoxy(Polyethylene glycol)-2000] that is useful in the manufacture of LPPs.

The term "HCAEC cell" refers to a human coronary artery endothelial cell.

The term "HUVEC cell" refers to a human umbilical vein endothelial cell.

The term "ROI" refers to a region of interest in a specified location in a subject. For example the ROI of a subject can be the heart of the subject.

The term "PET" refers to positron emission tomography. PET is a nuclear medicine imaging technique that can produce a three-dimensional image of ROIs in the body of a subject.

The term "ameliorating" refers to any therapeutically beneficial result in the treatment of a disease state, e.g., a heart disease state, including prophylaxis, lessening in the severity or progression, remission, or cure thereof.

The term "in situ" refers to processes that occur in a living cell growing separate from a living organism, e.g., growing in tissue culture.

The term "in vivo" refers to processes that occur in a living organism.

The term "mammal" as used herein includes both humans and non-humans and include but is not limited to humans, non-human primates, canines, felines, murines, bovines, equines, and porcines.

As used herein, the term "residue" refers to amino acids or analogs thereof.

As used herein, the term "peptide" refers to peptides, proteins, fragments of proteins, peptidomimetics, and the like that are comprised of more than one amino acid residue or similar molecule.

As used herein, "free C-terminus" refers to the C-terminal end of a peptide, and includes a peptide with a free carboxylic group or, as described in the Examples below, an amide terminated C-terminus, e.g., a —$CONH_2$ group.

As used herein, the term "peptidomimetic" refers to a peptide-like molecule that has the activity of the peptide upon which it is structurally based.

The term "isolated" refers to a peptide or peptidomimetic that is in a form that is substantially free from material such as contaminating polypeptides, lipids, nucleic acids, and other cellular material that can be associated with the peptide or peptidomimetic in a cell, or that is associated with the peptide or peptidomimetic in a library, or in a crude preparation such as a cell extract or cell lysate.

The term "selectively homes," as used herein in reference to a peptide, means that, in vivo, the targeting peptide localizes preferentially to a targeted tissue or cell as compared to most other tissues or vasculature. Selective targeting generally is characterized by at least a two-fold greater localization in the targeted tissue or cell as compared to other tissues or cells. A targeting molecule can be characterized by 5-fold, 10-fold, 20-fold, 30-fold, 40-fold, or more preferential localization to the targeted tissue or cell as compared to many or most non-targeted tissues or cells. It is understood that a targeting peptide can home, in part, to vasculature or tissue outside the targeted tissue or cells outside of the targeted tissue in addition to selectively targeting to targeted tissue.

The term percent "identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the percent "identity" can exist over a region of the sequence being compared, e.g., over a functional domain, or, alternatively, exist over the full length of the two sequences to be compared.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information (www.ncbi.nlm.nih.gov/).

The term "sufficient amount" means an amount sufficient to produce a desired effect, e.g., an amount sufficient to modulate protein aggregation in a cell.

The term "therapeutically effective amount" is an amount that is effective to ameliorate a symptom of a disease. A therapeutically effective amount can be a "prophylactically effective amount" as prophylaxis can be considered therapy.

It must be noted that, as used in the specification and the appended claims, the singular forms "a," "an" and "the" include plural referents unless the context clearly dictates otherwise.

Compositions of the Invention

The present invention relates to peptides which home to cells, e.g. heart cells, with high selectivity and which can be useful in the form of compositions. Such compositions can be used, e.g., for selectively targeting a systemically administered therapeutic or imaging agent to a cell. Compositions of the present invention are typically comprised of a peptide that includes a free terminus and a linked terminus, a particle, and a linking molecule that links the linked terminus of the peptide and the particle. In addition, compositions can further include compounds, agents, and/or labels. Selective targeting or homing of a compound increases the effective amount of the compound delivered to a cell or tissue while reducing the likelihood that the compound will have an adverse effect on other non-targeted cells, tissues, and/or organs. The present invention further relates to methods of using the compositions for imaging, e.g. PET imaging, and targeting cells, e.g. for delivering a therapeutic agent to one or more target cells in a subject.

Peptides

The peptides of the invention are typically provided in an isolated form and include a terminal arginine residue. Exemplary peptides of the present invention can include the amino acid sequences CRRRR (SEQ ID NO: 3), CRPPR (SEQ ID NO: 1), and/or CPPRR (SEQ ID NO: 2) at a terminus of the peptide. Typically the peptides of the present invention include the amino acid sequence PPR. The PPR amino acid sequence is typically at or near a terminus of the peptide. In one embodiment, the peptides can include a plurality of arginine residues at a terminus of the peptide, for example, the peptides can include 2 or more arginine residues at a terminus. In other embodiments, the peptides can include less than 10, 10, 11-19, 20, 21-29, 30, 31-39, 40, 41-49, 50, 51-59, 60, 61-69, 70, 71-19, 80, 81-89, 90 or more than 90 percent arginine residues. In another embodiment, the peptides of the present invention can have a net positive charge at a pH of 7.2.

The peptides of the invention can have a variety of lengths. A peptide of the invention can have, for example, a length of less than 5, 5, 6, 7, 8, 9, 10, 11, 12, 13, 14, 15, 16-19, 20, 21-24, 25, 26-29, 30, 31-34, 35, 36-39, 40, 41-44, 45, 46-49, 50, 51-59, 60, 61-69, 70, 71-79, 80, 81-89, 90, 91-99, 100, 101-500, 501-1000, 1001-5000, 5001-10000, or more than 10000 residues. A peptide of the invention can also be useful in the context of a significantly longer sequence.

The present invention provides peptides including linear, conformationally constrained, bifunctional, branched, and multivalent peptides and peptidomimetics. In addition peptides of the present invention can be dimerized. For example, the peptides can be dimerized through chemical bonds, covalent bonds, and/or non-covalent bonds. In one embodiment, as described herein, dimerization is via a disulfide bond between two cysteine residues.

An isolated peptide of the invention can include cyclic portions or be otherwise conformationally constrained. As used herein the term "conformationally constrained" means a molecule, such as a peptide, in which the three-dimensional structure is maintained substantially in one spatial arrangement over time. Conformationally constrained molecules can have improved properties such as increased affinity, metabolic stability, membrane permeability, or solubility. Methods of conformational constraint are well known in the art and can include, e.g., cyclization. The cyclization can be affected through a covalent or non-covalent bond. Intramolecular bonds can include, but are not limited to, backbone to backbone, side-chain to backbone, and side-chain to side-chain bonds. Methods of cyclization can include formation of a disulfide bond between the side-chains of non-adjacent amino acids or amino acid analogs; formation of a lactam bond, for example, between a side-chain group of one amino acid or analog thereof to the N-terminal amine of the amino-terminal residue; and formation of lysinonorleucine and dityrosine bonds.

The peptides of the present invention can also encompass peptidomimetics, as noted above. Peptidomimetics can include chemically modified peptides, peptide-like molecules comprising non-naturally occurring amino acids, and peptoids, and have an activity such as the selective targeting activity of the peptide upon which the peptidomimetic is derived and/or based (see, e.g., Goodman and Ro, Peptidomimetics for Drug Design, in "Burger's Medicinal Chemistry and Drug Discovery" Vol. 1 (ed. M. E. Wolff; John Wiley & Sons 1995), pages 803-861, herein incorporated by reference for all purposes). A variety of peptidomimetics are known in the art and can include, for example, peptide-like molecules which comprise a constrained amino acid, a non-peptide component that mimics peptide secondary structure, or an amide bond isostere. A peptidomimetic that includes a constrained, non-naturally occurring amino acid can include, for example, an α-methylated amino acid; αα-dialkylglycine or α-aminocycloalkane carboxylic acid; an Nα-Cα cyclized amino acid; an Nα-methylated amino acid; αβ- or γ-amino cycloalkane carboxylic acid; an αβ-unsaturated amino acid; a ββ-dimethyl or β-methyl amino acid; αβ-substituted-2,3-methano amino acid; an N—Cδ or Cα-Cδ cyclized amino acid; a substituted proline or another amino acid mimetic. A peptidomimetic which mimics peptide secondary structure can include, for example, a nonpeptidic β-turn mimic; γ-turn mimic; mimic of β-sheet structure; or mimic of helical structure, each of which is well known in the art. A peptidomimetic can also be a peptide-like molecule which includes, for example, an amide bond isostere such as a retro-inverso modification; reduced amide bond; methylenethioether or methylene-sulfoxide bond; methylene ether bond; ethylene bond; thioamide bond; trans-olefin or fluoroolefin bond; 1,5-disubstituted tetrazole ring; ketomethylene, or fluoroketomethylene bond, or another amide isostere. These and other peptidomimetics are encompassed within the meaning of the term "peptidomimetic", as used herein.

The present invention further provides a composition including a particle linked, by a linking molecule, to a peptide that selectively homes to a tissue, e.g. heart vasculature. Particles of the present invention are discussed in more detail below. In such a composition, the peptide can home to the tissue in vivo with selectivity, for example, of at least 5-fold relative to a particle with no linked peptide, and can be, for example, a peptide described above. In related aspects the selectivity can be at least 10, 20, 30, 40, 50, 60, 70, 80, 90 or more fold relative to a particle with no linked peptide. In one embodiment, a composition of the invention includes a peptide comprising one or more of the amino acid sequences CRPPR (SEQ ID NO: 1), CRRRR (SEQ ID NO: 3), CPPRR (SEQ ID NO: 2), or conservative variants or peptidomimetics thereof. Typically the peptides of the present invention bind to one or more scavenger receptors on the target tissue or cell.

In some embodiments, a composition of the invention includes a plurality of peptides. For example, the composition can include two or more, three or more, five or more, ten or more, twenty or more, thirty or more, forty or more, fifty or more, 100 or more, 200 or more, 300 or more, 400 or more, 500 or more, 1000 or more, 2000 or more, 3000 or more, 4000 or more, 5000 or more, or 6000, or 6000 or more peptides that selectively home to a target tissue or cell, e.g., the heart. Typically, the peptides can include from less than 1 to more than 10 mol percent of the composition. In other embodiments, the peptides can include 2, 3, 4, 5, 6, or 7 mol percent of the composition. In another embodiment, the plurality of peptides can have identical amino acid sequences. In another embodiment, the plurality of peptides can include distinct amino acid sequences. In a further embodiment, the composition includes peptides having non-identical amino acid sequences.

The peptides of the present invention can be generated using any method available to one of ordinary skill in the art. For example, peptides can be generated wholly or partly by chemical synthesis. The peptides of the invention can be readily prepared according to well-established, standard liquid or solid-phase peptide synthesis methods, general descriptions of which are broadly available (see, for example, in J. M. Stewart and J. D. Young, Solid Phase Peptide Synthesis, 2nd edition, Pierce Chemical Company, Rockford, Ill. (1984), in M. Bodanzsky and A. Bodanzsky, The Practice of Peptide Synthesis, Springer Verlag, N.Y. (1984); and Applied Biosystems 430A Users Manual, ABI Inc., Foster City, Calif.), or they can be prepared in solution, by the liquid phase method or by any combination of solid-phase, liquid phase and solution chemistry, e.g. by first completing the respective peptide portion and then, if desired and appropriate, after removal of any protecting groups being present, by introduction of a residue by reaction of the respective carbonic or sulfonic acid or a reactive derivative thereof.

The peptides can also be obtained by methods well-known in the art for peptide purification and recombinant peptide expression. For recombinant expression of one or more of the peptides, the nucleic acid containing all or a portion of the nucleotide sequence encoding the PTH peptide can be inserted into an appropriate expression vector (i.e., a vector that contains the necessary elements for the transcription and translation of the inserted peptide coding sequence). In one embodiment, the regulatory elements are heterologous (i.e., not the native gene promoter). Alternately, the necessary transcriptional and translational signals can also be supplied by the native promoter for the genes and/or their flanking regions.

The peptides can also be purified from a natural source. Depending on the source, the peptide can be brought into a solution by breaking the tissue or cells containing it. There are several methods to achieve this, including: repeated freezing and thawing, sonication, homogenization by high pressure or permeabilization by organic solvents. The method of choice typically depends on how fragile the peptide is and how sturdy the cells are. After this extraction process soluble peptide will be in the solvent, and can be separated from cell membranes, DNA, etc. by centrifugation. After the extraction process the peptide of interest can be further purified using methods known in the art including precipitation, differential solubilization, ultracentrifugation, and/or chromatography methods including size exclusion, ion exchange, high pressure liquid, and immunoaffinity.

Particles

The composition of the present invention further includes particles for carrying compounds. Particles useful in a composition of the present invention that are linked, by a linking molecule, to peptides can include, but are not limited to: phage; retroviruses; adenoviruses; adeno-associated viruses and other viruses; cells; liposomes; phospholipid-based liposomes; polymeric matrices; lipid formulations; phospholipid-based formulations; micelles; fatty acid formulations; microbubbles; caveolae; non-polymeric matrices or particles such as, e.g., gold particles; microdevices; nanodevices; and nano-scale semiconductor materials. Typically, the compositions of the present invention include at least one lipid or at least one fatty acid.

In one embodiment of the present invention, the use of lipid formulations of particles, e.g. liposomes, is contemplated for the introduction of a compound to a subject of interest. Compounds of the present invention are described in more detail below. In a specific embodiment of the invention, the compound can be associated with, linked to, inserted into, carried by, or attached to a membrane, outer surface, lipid, or lipid membrane of the particle. In other embodiments, the compound associated with a lipid of the particle can be attached to a liposome via a linking molecule that is associated with both the liposome and the particle. The linking molecule is described in more detail below.

Lipids are fatty substances which can be naturally occurring or synthetic. For example, lipids include the fatty droplets that naturally occur in the cytoplasm as well as the class of compounds which are well known to those of skill in the art that contain long-chain aliphatic hydrocarbons and their derivatives, such as phospholipids, fatty acids, alcohols, amines, amino alcohols, and aldehydes. Additional examples of suitable lipids include hydrogenated lecithin from plants and animals, such as egg yolk lecithin and soybean lecithin. The lipid can also be phosphatidyl choline produced from partial or complete synthesis containing mixed acyl groups of lauryl, myristoyl, palmitoyl and stearoyl. Lipids can include, e.g., 1,2-Dipalmitoyl-snglycero-3phosphocholine (DPPC).

"Liposome" is a generic term encompassing a variety of single and multilamellar lipid particles formed by the generation of enclosed lipid bilayers or aggregates. Liposomes can be characterized as having vesicular structures with a phospholipid bilayer membrane and an inner aqueous medium. Multilamellar liposomes can have multiple lipid layers separated by aqueous medium. Typically, they form spontaneously when phospholipids are suspended in an excess of aqueous solution. The lipid components typically undergo self-rearrangement before the formation of closed structures and entrap water and dissolved solutes between the lipid layers. However, the present invention also encompasses compositions that have different structures in solution than the normal vesicular structure. For example, the lipids can assume a micellar structure or merely exist as nonuniform aggregates of lipid molecules. Also contemplated are lipofectamine-agent complexes. The liposome is one example of a particle of the present invention.

A neutrally charged lipid can comprise a lipid with no charge, a substantially uncharged lipid, or a lipid mixture with equal number of positive and negative charges. Suitable phospholipids include phosphatidyl cholines and others that are well known to those of skill in the art.

Phospholipids can be used for preparing the liposomes according to the present invention and can carry a net positive, negative, or neutral charge. For example, diacetyl phosphate can be employed to confer a negative charge on the liposomes, and stearylamine can be used to confer a positive charge on the liposomes. The liposomes can typically be made of one or more phospholipids.

Phospholipids can form a variety of structures other than liposomes when dispersed in water, depending on the molar ratio of lipid to water. At low ratios the liposome is a preferred structure. The physical characteristics of liposomes can depend on pH, ionic strength, and/or the presence of divalent cations. Liposomes can show low permeability to ionic and/or polar substances, but at elevated temperatures undergo a "phase transition" which markedly alters their permeability. Suitable phospholipids include, for example, dimyristoylphosphatidyl choline, palmitoylmyristoylphosphatidyl choline, myristolypalmitoylphosphatidyl choline, dipalmitoylphosphatidyl choline, stearoylpalmitoylphosphatidyl choline, palmitoylstearolyphosphatidyl choline, and distearolyphosphatidyl choline. Another suitable phospholipid is a synthetic $C_{17}$ phosphatidyl choline from Aventi Inc.

The compositions of the present invention are not limited to any particular structure in solution prior to administration to a subject. For example, they can be present in a bilayer structure, such as liposome; as micelles, or with a collapsed structure. They can also simply be interspersed in a solution, possibly forming aggregates which are not uniform in either size or shape.

It should be appreciated that membrane-forming material of a liposome can be any lipid or fatty acid comprising material. Exemplary materials which may form a membrane include, but are not limited to, natural lipids, synthetic lipids, phospholipids, or microbial lipids.

Liposomes can interact with cells via four different mechanisms: Endocytosis by phagocytic cells of the reticuloendothelial system such as macrophages and/or neutrophils; adsorption to the cell surface, either by nonspecific weak hydrophobic and/or electrostatic forces, and/or by specific interactions with cell-surface components; fusion with the plasma cell membrane by insertion of the lipid bilayer of the liposome into the plasma membrane, with simultaneous release of liposomal contents into the cytoplasm; and/or by transfer of liposomal lipids to cellular and/or subcellular membranes, and/or vice versa, without any association of the liposome contents. Varying the liposome formulation can alter which mechanism is operative, although more than one may operate at the same time.

The size of the liposomes varies depending on the method of synthesis. In one aspect, liposomes are from less than or equal to about 1 nm, 10 nm, 50 nm, 100 nm, 120 nm, 130 nm, 140 nm, or 150 nm, up to about 175 nm, 180 nm, 200 nm, 250 nm, 300 nm, 350 nm, 400 nm, 500 nm, 1 μm, 10 μm, 100 μm, 1000 μm or more in diameter. A liposome suspended in an aqueous solution is generally in the shape of a spherical vesicle, having one or more concentric layers of lipid bilayer molecules. Each layer consists of a parallel array of molecules represented by the formula XY, wherein X is a hydrophilic moiety and Y is a hydrophobic moiety. In aqueous suspension, the concentric layers are arranged such that the hydrophilic moieties tend to remain in contact with an aqueous phase and the hydrophobic regions tend to self-associate. For example, when aqueous phases are present both within and outside the liposome, the lipid molecules may form a bilayer, known as a lamella, of the arrangement XY-YX. Aggregates of lipids can form when the hydrophilic and hydrophobic parts of more than one lipid molecule become associated with each other. The size and shape of these aggregates will depend upon many different variables, such as the nature of the solvent and the presence of other compounds in the solution.

Liposomes used according to the present invention can be made by different methods known to those of ordinary skill in the art. Liposomes within the scope of the present invention can be prepared in accordance with known laboratory techniques. In one embodiment, liposomes are prepared as described in the Example, below. In another embodiment, liposomes are prepared by mixing liposomal lipids, in a solvent in a container, e.g., a glass, pear-shaped flask. The container can have a volume ten-times greater than the volume of the expected suspension of liposomes. Using a rotary evaporator, the solvent can be removed at approximately 40° C. under negative pressure. The solvent normally is removed within about 5 min. to 2 hours, depending on the desired volume of the liposomes. The composition can be dried further in a desiccator under vacuum. The dried lipids generally are discarded after about 1 week because of a tendency to deteriorate with time.

Dried lipids can be hydrated at, e.g., approximately 25-50 mM phospholipid in sterile, pyrogen-free water by shaking until all the lipid film is resuspended. The aqueous liposomes can be then separated into aliquots, each placed in a vial, lyophilized and sealed under vacuum.

In the alternative, liposomes can be prepared in accordance with other known laboratory procedures: the method of Bangham et al. (1965), the contents of which are incorporated herein by reference; the method of Gregoriadis, as described in Drug Carriers in Biology and Medicine, G. Gregoriadis ed. (1979) pp. 287-341, the contents of which are incorporated herein by reference; the method of Deamer and Uster, 1983, the contents of which are incorporated by reference; and the reverse-phase evaporation method as described by Szoka and Papahadjopoulos, 1978. The aforementioned methods differ in their respective abilities to entrap aqueous material and their respective aqueous space-to-lipid ratios, and each is incorporated by reference for all purposes.

The dried lipids or lyophilized liposomes prepared as described above can be dehydrated and reconstituted in a solution of inhibitory peptide and diluted to an appropriate concentration with a suitable solvent. The mixture is then vigorously shaken in a vortex mixer. Contaminates are removed by centrifugation at 29,000×g and the liposomal pellets washed. The washed liposomes are resuspended at an appropriate total phospholipid concentration, e.g., about 50-200 mM.

In addition to the above, micelles within the scope of the present invention can be prepared in accordance with known laboratory techniques. For example, micelles can be prepared in accordance with the methods of: J. M. Seddon, R. H. Templer. *Polymorphism of Lipid-Water Systems*, from the Handbook of Biological Physics, Vol. 1, ed. R. Lipowsky, and E. Sackmann. (c) 1995, Elsevier Science B.V. ISBN 0-444-81975-4., the contents of which are incorporated by reference; S. A. Baeurle, J. Kroener, Modeling effective interactions of micellar aggregates of ionic surfactants with the Gauss-Core potential, J. Math. Chem. 36, 409-421 (2004)., the contents of which are incorporated by reference; McBain, J. W., Trans. Faraday Soc. 1913, 9, 99., the contents of which are incorporated by reference; Hartley, G. S., Aqueous Solutions of Paraffin Chain Salts, A Study in Micelle Formation, 1936, Hermann et Cie, Paris., the contents of which are incorporated by reference.

Linking Molecules

The composition of the present invention further includes linking molecules useful for linking particles and peptides of the present invention. The term "linking molecule" refers to a substance capable of linking with the particles of the invention and also capable of linking to a linked terminus of a peptide of the invention. Examples of linking molecules include: nucleic acid molecules, lipids, glycols, peptides, polymers, copolymers, polymerizable coupling agents, silica, proteins, and chain-like molecules having a surface with the opposed polarity with respect to the particles. Nucleic acids can provide a link to peptides containing themselves nucleic acid molecules, though with a complementary sequence with respect to the linking molecule. Polymerizable coupling agents can include diacetylene, styrene butadiene, vinylacetate, acrylate, acrylamide, vinyl compounds, styrene, silicone oxide, boron oxide, phosphorous oxide, borates, pyrrole, polypyrrole and phosphates. An exemplary example of a linking molecule of the present invention includes polyethylene glycol (PEG).

As used herein, "PEG" refers to polyethylene glycol. As used herein, the terms "polyethylene glycol" and "PEG" broadly encompass any polyethylene glycol molecule known in the art. Polyethylene glycol is typically a water-soluble polymer that is commercially available or can be prepared by ring-opening polymerization of ethylene glycol according to methods well known in the art (see Kodera, Y., et al., Progress in Polymer Science 23 (1998) 1233-1271; Francis, G. E., et al., Int. J. Hematol. 68 (1998) 1-18). The number of ethylene glycol units in PEG is approximated for the molecular mass described in Daltons. For example, if two PEG molecules are attached to a peptide where each PEG molecule has the same molecular mass of 10 kDa, then the total molecular mass of PEG on the peptide is about 20 kDa. The molecular masses of the PEG attached to the peptide can also be different, e.g., of two molecules on a peptide one PEG molecule can be 5 kDa and one PEG molecule can be 15 kDa. It is well known in the art that a PEG linking molecule can be lengthened to a desired length by one of ordinary skill in the art by adding additional PEG molecule together. In some embodiments, the PEG linking molecule can be 3600 $M_w$.

In one embodiment, the PEG linking molecule can be either linear or branched. Branched PEGs are described, e.g., in Veronese, F. M., et al., Journal of Bioactive and Compatible Polymers 12 (1997) 196-207. Branched PEGs can be prepared, for example, by the addition of polyethylene oxide to various polyols, including glycerol, pentaerythriol, and sorbitol. For example, a four-armed branched PEG can be prepared from pentaerythriol and ethylene oxide. Branched PEGs usually have 2 to 8 arms and are described in, for example, U.S. Pat. No. 5,932,462. PEGs with two PEG sidechains linked via the primary amino group of a lysine can also be used in the present invention as a linking molecule (Monfardini, C., et al., Bioconjugate Chem. 6 (1995) 62-69).

In another embodiment, the linking molecule is linked to the peptide using a linking agent prior to linking the linking molecule to the particle. Linking agents can include, e.g., HBTU. In other embodiments, the linking molecule is linked to the particle prior to linking the linking molecule to the peptide. In one example, a PEG linking molecule is linked to the peptide. Following linkage of the PEG linking molecule and the peptide, the linking molecule is further linked to a lipid to produce a lipo-PEG-peptide (LPP). In one aspect of the present invention, the LPP can be used in the generation of a particle, e.g., a liposome using methods known in the art and described in detail above.

In other examples, protocols for coupling reactions of linking molecules to peptides can be found in the literature, for instance in "Bioconjugate Techniques" (Greg T. Hermanson, Academic Press 1996), herein incorporated by reference. The peptide can be coupled to the linking molecule, chemically, covalently or non-covalently, in line with standard procedures of organic chemistry such as oxidation, halogenation, alkylation, acylation, addition, substitution, or amidation. These methods for coupling a peptide to the covalently or non-covalently bound linking molecule can be applied prior to the coupling of the linking molecule to the particle or thereafter. In addition, these methods of coupling a peptide and a linking molecule can also be used for linking the particle and the linking molecule. Further, it is possible, by means of incubation, to effect a direct binding of peptides to correspondingly pre-treated particles (for instance by trimethylsilyl bromide), which display a modified surface due to this pre-treatment (for instance a higher charge or polar surface). Other linking methods for linking peptides and/or particles to linking molecules are generally known to one of ordinary skill in the art.

Compounds

Compounds suitable for use in the present invention include small molecules, therapeutic agents and pharmacologically active agents, nutritional molecules, cosmetic agents, diagnostic agents, labels, and imaging agents. Compounds can also include nucleic acids, e.g., genes, siRNA, microRNA, viruses, vectors, or gene fragments. Typically the composition of the present invention includes the compound. In general, the amount of the particular compound carried by the particle is selected according to the desired therapeutic dose and/or the unit dose. Suitable therapeutic agents of the present invention can include, for example, antineoplastics, monomethylauristatin E, monomethylauristatin F, antitumor agents, antibiotics, antifungals, anti-inflammatory agents, immunosuppressive agents, anti-infective agents, antivirals, anthelminthic, antiparasitics, angiogenic agents, anti-thrombotic agents, anti-inflammatory agents, immunosuppressive agents, anti-arrhythmic agents, tumor necrosis factor inhibitors, endothelin inhibitors, angiotensin-converting enzyme (ACE) inhibitors, calcium antagonists, statins, beta blockers, blood thinners, antibiotic agents, antiviral agents, and viral vectors. Exemplary examples of compounds of the present invention include amnioterone and digoxin.

In view of the above, it is understood that a variety of therapeutic agents can be useful for treating a cardiovascular disease according to a method of the invention. Useful therapeutic agents for treating cardiovascular diseases include angiogenic agents, anti-thrombotic agents, anti-inflammatory agents, immunosuppressive agents, anti-arrhythmic agents, tumor necrosis factor inhibitors, endothelin inhibitors, angiotensin-converting enzyme inhibitors, calcium antagonists, antibiotic agents, antiviral agents and viral vectors. One skilled in the art understands that these as well as additional known or other therapeutic agents can be selectively directed to heart vasculature when incorporated into a composition or method of the invention. Furthermore, one skilled in the art of medicinal cardiology understands that these and other therapeutic agents can be used separately or together in the compositions and methods of the invention.

In another embodiment of the present invention, the particle can carry an imaging agent detectable by means such as e.g., color, fluorescence, radiation, or electromagnetic signals. Imaging agents will typically include, but are not limited to, fluorescent moieties, chemiluminescent moieties, particles, enzymes, dyes, radiolabels, quantum dots, light emitting moieties, light absorbing moieties, and intercalating dyes including propidium iodide and ethidium bromide and the cyanine dyes. Imaging agents suitable for use in the present invention are compounds that are generally capable of producing, either directly or indirectly, a detectable signal. Some examples of the types of imaging agents that can be used with the methods of the invention include, e.g., fluorescent or colored dyes, isotopic labels, enzymes, immune labels (e.g., antibodies or antigens), gold particles, fluorophores, magnetic particles, and quantum dots. The imaging agents can be incorporated into a particle. The imaging agents can be attached to a particle. The imaging agents can be carried by a particle. The imaging agent can directly or indirectly provide a detectable signal. Any method known in the art for conjugating and/or binding an imaging agent to a particle can be used.

In one embodiment, fluorescent labels are used as imaging agents. Fluorescent or chemiluminescent imaging agents that can be used are, e.g., fluorescein isothiocyanate, rhodamine, and luciferin. In another embodiment, the imaging agents are radiolabels, e.g., $^3$H, $^{125}$I, $^{35}$S, $^{14}$C, $^{18}$F, [$^{18}$F]FDP, $^{64}$Cu, or $^{32}$P. One of skill in the art will appreciate that the imaging agent can be an enzyme (e.g., horse radish peroxidase, alkaline phosphatase, beta-galactosidase and others commonly used in, e.g., an ELISA); biotin for staining with labeled streptavidin conjugate; magnetic beads, and labels such as colloidal gold or colored glass or plastic (e.g., polystyrene, polypropylene, latex, etc.) beads.

In another embodiment, the particle can be associated with a plurality of compounds. The plurality can include 2, 3, 4, 5, 6, 7, 8, 9, 10 or more compounds, as is deemed necessary by one of ordinary skill for using the present invention.

In some embodiments, a compound can be coupled to a particle through a chemically reactive group. In other aspects, a compound can be attached to a particle during synthesis of the particle or incorporated on the particle after particle synthesis.

Methods of the Invention

Methods for Targeting Cells with Compositions

Methods of the present invention can be used for targeting cells or tissues in a subject using the compositions of the present invention. In general these methods can be used for therapeutic applications and/or imaging applications, e.g. PET imaging, in a subject by injection and/or administration to the subject. In one aspect of the methods for therapeutic and imaging applications, a variety of routes of administration are useful in the methods of the invention. Such routes encompass systemic and local administration and include, without limitation, oral administration, intravenous injection, intraperitoneal injection, intramuscular injection, subcutaneous injection, transdermal diffusion or electrophoresis, local injection, and extended release delivery devices including locally implanted extended release devices such as bioerodible or reservoir-based implants. Typically, following administration and/or injection, the compositions will home to or target the cell or tissue of interest in the subject.

Diseases and Conditions

The methods of the invention can be useful for treating a variety disease types in a given subject, e.g. a human. Diseases treated by the methods of the present invention can include ischemic conditions, cardiopathies, cardiovascular diseases, and brain diseases including cancer. For example, cardiopathies and cardiovascular diseases include, but are not limited to, coronary artery disease (CAD); atherosclerosis; thrombosis; restenosis; vasculitis including autoimmune and viral vasculitis such as polyarteritis nodosa, Churg-Strass syndrome, Takayasu's arteritis, Kawasaki Disease and Rickettsial vasculitis; atherosclerotic aneurisms; myocardial hypertrophy; congenital heart diseases (CHD); ischemic heart disease and anginas; acquired valvular/endocardial diseases; primary myocardial diseases including myocarditis; arrhythmias; and transplant rejection. Cardiopathies and cardiovascular diseases to be treated according to a method of the invention further include, but are not limited to, metabolic myocardial diseases and myocardiomyopathies such as congestive, hypertrophic and restrictive cardiomyopathies, and heart transplants. In this example, a composition of the invention will typically concentrate in the heart blood vessels and can further accumulate in the myocardium. Thus, the compositions and methods of the invention are useful for treating these and other disorders of heart blood vessels or myocardium.

Cells

Cells typically targeted by the methods of the present invention can include a mammalian cell, a human cell, a cardiac cell, an endothelial cell, a cardiac endothelial cell, a HCAEC cell, a HUVEC cell, a brain cell, or a cancer cell. Other cells are contemplated by the present invention and can include bacterial cells, yeast cells, primate cells, non-mammalian cells, and non-human cells.

Positron Emission Tomography (PET) Imaging of Compositions

PET imaging can be used in the methods of the invention for imaging compositions targeted to a target tissue or cell in a subject. PET is a technique for measuring the concentrations of positron-emitting isotopes within the tissues of a subject, e.g. a human. These measurements are, typically, made using PET cameras outside of the subject. PET can be broken down into several steps including, but not limited to, synthesizing a composition of the present invention to include a positron-emitting isotope (described above and below); administering the isotopically labeled composition to a subject; and imaging the distribution of the positron activity as a function of time by emission tomography. PET is described, for example, by Alavi et al. in Positron Emission Tomography published by Alan R. Liss, Inc. in 1985.

Positron-emitting isotopes used in PET can include, but are not limited to, Carbon-11, Nitrogen-13, Oxygen-15, and Fluorine-18. Typically, positron-emitting isotopes can have short half-lives to help minimize the long term radiation exposure that a subject receives from high dosages required during PET imaging.

In some aspects, PET imaging can be used to measure the binding kinetics of compositions of the present invention with receptors, e.g. scavenger receptors. For example, administering an isotopically labeled composition of the present invention that penetrates into a subject and binds to a receptor creates a baseline PET signal which can be monitored while administering a second, different, non-isotopically labeled compound. The baseline PET signal will decrease as the non-isotopically labeled compound competes for the binding to the receptor.

In general, compositions useful in performing PET are those which exhibit high selectivity and modest affinity to a receptor, and are eventually metabolized.

Delivery of Compounds to the Brain of a Subject

The compositions of the present invention can be used to deliver compounds to the brain of a subject. In one embodiment, the composition used for compound delivery to the brain of a subject is a liposome including lipids with glycerol head groups. In another embodiment, the liposome includes a radiotracer. In another embodiment the liposome can include a compound. In another embodiment the liposome can include a plurality of compounds and/or radiotracers. In another embodiment the release of compounds in the brain of the subject is time-specific.

In one aspect of the method of delivering compounds to the brain of a subject, the liposomes are trapped by the liver. In another aspect the liposomes are decomposed into lipids. In another related aspect, the decomposed liposome lipids are further decomposed into fatty acids and glycerol analogs comprising a compound.

In another aspect of the method, the glycerol analog can enter the blood pool of the subject. In another aspect, the glycerol analog can accumulate in the brain of the subject. The transport of glycerol into the brain has been studied previously. See Gidez L I, Karnovsky M L. The Metabolism of C-14 Glycerol in the Intact Rat. J Biol Chem 1954; 206(1): 229-242.; McKenna M C, Tildon J T, Bezold L I. Glycerol Oxidation in Discrete Areas of Rat-Brain from Young, Adolescent, and Adult-Rats. J Neurosci Res 1988; 20(2):224-230.; Sloviter H A, Shimkin P, Suhara K. Glycerol as a Substrate for Brain Metabolism. Nature 1966; 210(5043):1334.; Waterhou. J m, Coxon R V. Entry of Glycerol into Brain Tissue. J Neurol Sci 1970; 10(3):305.

Pharmaceutical Compositions of the Invention

Methods for treatment of diseases, e.g. heart or brain diseases are also encompassed by the present invention. Said methods of the invention include administering a therapeutically effective amount of the composition described in more detail above. The composition of the invention can be formulated in pharmaceutical compositions. These compositions can comprise, in addition to one or more of the compositions, a pharmaceutically acceptable excipient, carrier, buffer, stabiliser or other materials well known to those skilled in the art. Such materials should be non-toxic and should not interfere with the efficacy of the active ingredient. The precise nature of the carrier or other material can depend on the route of administration, e.g. oral, intravenous, cutaneous or subcutaneous, nasal, intramuscular, intraperitoneal routes.

Pharmaceutical compositions for oral administration can be in tablet, capsule, powder or liquid form. A tablet can include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol can be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic particles such as Sodium Chloride Injection, Ringer's Injection, and Lactated Ringer's Injection. Preservatives, stabilisers, buffers, antioxidants and/or other additives can be included, as required.

Administration of the composition is typically in a "therapeutically effective amount" or "prophylactically effective amount" (as the case can be, although prophylaxis can be considered therapy), this being sufficient to show benefit to the individual. The actual amount administered, and rate and time-course of administration, will depend on the nature and severity of protein aggregation disease being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 16th edition, Osol, A. (ed), 1980.

A composition can be administered alone or in combination with other treatments, either simultaneously or sequentially dependent upon the condition to be treated.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences*, 18th Edition (Easton, Pa.: Mack Publishing Company, 1990); Carey and Sundberg *Advanced Organic Chemistry* $3^{rd}$ *Ed.* (Plenum Press) Vols A and B(1992).

Methods

Targeted-Liposome Preparation

Peptide Synthesis

Protected 9-fluorenylmethyloxycarbonyl (Fmoc) amino acids and coupling agents (O-(7-azabenzotriazol-1-yl)-1,1,3,3-tetramethyluronium hexafluorophosphate (HATU) and O-benzotriazolyl-N',N',N',N'-tetramethyluronium hexafluorophosphate (HBTU)) were purchased from GL Biochem (Shanghai) Ltd. Fmoc-PAL-PEG-PS resin (0.16-0.21 mmol/g) was from Applied Biosystems (Foster City, Calif.). Solvents and other agents were all of analytical purity and from Sigma-Aldrich (Milwaukee, Wis.) and VWR (Brisbane, Calif.). The following amino acid side chain protections were used: t-But (Asp), Pbf (Arg), Trt (Cys), Mmt(Lys) and OAll (Glu) (Applied Biosystems). Five peptides were synthesized in this paper: CRPPR (SEQ ID NO: 1), CPPRR (SEQ ID NO: 2), CRRPP (SEQ ID NO: 7), CRRRR (SEQ ID NO: 3) and c(RGDY(OMe)KE) (SEQ ID NO: 6). For c(RGDY(OMe)KE) (SEQ ID NO: 6), after the linear peptide Fmoc-R(Pbf)GD(But)Y(OMe)K(Mmt)E(OAll) (SEQ ID NO: 6) was synthesized, OAll was removed with catalyst Pd, Fmoc was removed with 20% piperidine in dimethylformamide, and head-to-tail cyclization was performed. Mmt was removed by 1% trifluoroacetic acid (TFA) in dichloromethane (DCM) to produce a free amino group on lysine for further coupling. After peptide synthesis, part of the peptidyl resin was cleaved from the resin using 94% TFA, 1.0% triisopropylsilane (TIPS), 2.5% ethanedithiol (EDT), and 2.5% water followed by precipitation with diethylether (for c(RGDY(OMe)KE) (SEQ ID NO: 6), TFA:TIPS:Water=95:2.5:2.5 was used). The products were purified using reversed-phase high performance liquid chromatography (HPLC). Matrix Assisted Laser Desorption Ionisation time-of-flight (MALDI-TOF) mass spectrometry (MS) confirmed the mass of the free peptide measured with the ABI-4700 TOF-TOF (Applied Biosystems) using matrix Sinapic acid with 3 layer sample preparation method [26]. Reversed-phase HPLC was performed using a Phenomenex Jupiter 4µ Proteo 90A (250×4.6 mm, analytical), and a Phenomenex Jupiter 10µ Proteo 90A (250×21.2 mm, preparative) with a gradient from 10-90% B in 30 min (solvent A: 0.05% TFA, solvent B: 0.05% TFA/acetonitrile 10:90 (v/v)) and a flow rate of 1.5/15 ml/min for analytical/preparative column.

Lipo-PEG-Peptide (LPP) Synthesis

Fmoc-NH-(PEG)27-COOH and Fmoc-Lys(Fmoc)-OH were purchased from Novabiochem (Darmstadt, Germany) and Stearic Acid was purchased from Sigma-Aldrich. Polyethylene glycol (PEG) was coupled onto peptidyl resin with HBTU as the coupling agent, which was repeated until the expected PEG length was reached. After finishing the pegylation step, Fmoc-Lys(Fmoc)-OH and stearic acid were coupled in sequence. LPPs (FIG. 1a) were cleaved from resin and purified with HPLC and molecular weights were confirmed with MALDI-TOF MS. Yields were 20% and 12% for linear and cyclic peptides. For a cysteine containing LPP, dimerization was carried out as described in [27]. LPP were dissolved in 0.01 M ammonium bicarbonate at a concentration of 1-2 mM and the solution was left open to the air and stirred. The reaction was monitored with HPLC until all of the monomer reacted, which normally requires less than 4 hours. Our initial in vitro experiments showed that dimerization could enhance targeting (data not shown); therefore we used the dimerized LPP in this work. Molar fractions were calculated based on the peptides prior to dimerization.

Preparation of [18F]FDP and Fluorescently-Labeled Liposomes 1,2-dipalmitoyl-snglycero-3-phosphocholine (DPPC), 1,2 distearoyl-sn-glycero-3-phosphoethanolamine-N-[Methoxy (Polyethylene glycol)-2000] (DSPE-PEG2000), and a mini-extruder were purchased from Avanti Polar Lipids Inc. (Alabaster, Ala.). An appropriate amount of DPPC, DSPE-PEG2000, and LPP in chloroform was mixed and chloroform was removed by lyophilization.

[18F]FDP Liposomes: The lipid mixture was resuspended with 20 mM PBS buffer (pH 7.4) and added to the fresh prepared [18F]FDP. The solution was sonicated at 60° C. for 1 min, and extruded through polycarbonate membranes at 60° C. (21 passes through 100-nm-diameter pore membrane) and then the extruded liposomes were purified with Sephadex G-50 columns (GE Healthcare, NJ) to obtain the radiolabeled targeted liposomes (FIG. 1b). After the radioactivity decayed, the liposomal size distribution was measured with the Nanotrac (Microtrac Inc., FL), and the zeta potential was characterized by the Zeta Potential/Particle Sizer Nicomp™ 380ZLS (Particle Sizing Systems, CA). The phospholipid concentration was tested with the Phospholipids C kit (Wako Chemicals USA, Inc., VA) and the LPP concentration was measured by HPLC.

Fluorescent Liposomes: liposome synthesis was as above except that the fluorescent dye Alexa 555 (Invitrogen Corporation, Carlsbad, Calif.) was dissolved into the buffer at a concentration of 0.3 mM, and the labeled buffer was used to resuspend the dried lipid mixture. After sonication and extrusion, the liposomes were purified with a G-75 column (GE Healthcare, NJ).

In Vitro Incubation and Internalization

Binding and internalization of NON-, CRPPR- (SEQ ID NO: 1), CPPRR- (SEQ ID NO: 2) and CRRPP- (SEQ ID NO: 7) targeted liposomes were studied with a malignant melanoma cell line, A375 (American Type Culture Collection, Manassas, Va.), and an endothelial cell line, Human Coronary Artery Endothelial Cells (HCAEC, Lonza, N.J.). Cells were seeded at ~4.8×104 cells per dish on 60 mm petri dishes and were grown to approximately 90% confluency. To each dish, calcein (Sigma-Aldrich)-loaded liposomes were added with final concentrations of lipids and calcein in media of ~0.5-0.9 mg/ml and 0.75-1.25 mM, respectively. Cells were incubated at 37° C. in 5% CO2 for 16 hours; including a wash after 2 hours to remove liposomes. Then, cells were collected via trypsinization with 0.05% trypsin-EDTA (Invitrogen). Flow cytometry was performed using a FACScan flow cytometer and CELLQuest software (Becton Dickinson, Franklin Lakes, N.J.) for calcein. For each sample, 20,000 gated events were collected in low-speed mode at a collection rate of approximately 100 counts per second and mean fluorescence intensity quantified.

Animal Studies

All animal studies were conducted under a protocol approved by the University of California, Davis Animal Use and Care Committee (Davis, Calif.). A total of 160 animals (male FVB mice, 8-12 weeks, 25-30 g, Charles River, Mass.) were examined over the course of this study, with four animals imaged with each day's formulation. In order to detect a difference between groups (as compared with the heart targeting of CRPPR-3 ('CRPPR' disclosed as SEQ ID NO: 1) without an inhibitor), 4, 8, or 12 animals were studied to detect an expected difference of 30, 20 or 17%, respectively, based on preliminary data (not shown), using a power of 0.8 and alpha error level of 0.05. All mice were housed four animals per cage in a 12 hour light cycle environment and allowed access to water and a standard mouse diet. For all procedures, induction of anesthesia was achieved at 3.0-3.5% isoflurane (Halocarbon Laboratory, River Edge, N.J.) and maintained at 2.0-2.5%. Respiratory rate and temperature were monitored throughout each procedure to ensure proper levels of anesthesia and comfort. Body temperature was maintained by placing the animals on a heating pad during all procedures and scans. The mice were catheterized to ensure proper injection of lipid formulations, after which bolus injections of [18F]FDP-labeled liposomes (0.05 mg lipids, 2 mg lipids per kg of body weight, mg/kg) were administered as PET scans were initiated, using a manually-controlled injection that was timed for uniform administration over 15 seconds.

Positron Emission Tomography (PET) Scans and Time-Activity Curves (TAC)

PET, a nuclear medicine medical imaging technique producing a three-dimensional image of radiotracer concentration over time, was employed to study the pharmacodynamics of injected liposomes. PET scans were conducted with micro-PET Focus (Siemens Medical Solutions, Knoxyille, Tenn.) over 90 minutes and maximum a posteriori (MAP) files were created with ASIPro software (Siemens Medical Solutions, Knoxyille, Tenn.) and used to obtain quantitative activity levels in each organ of interest as a function of time. TACs were obtained with region-of-interest (ROI) analysis using ASIPro software and expressed as percentage of injected dose per cubic centimeter (% ID/cc).

Well Counts

After the PET scans, the mice were euthanized by cervical dislocation and organs of interest were harvested and radioactivity measured using a 1470 Automatic Gamma Counter (Perkin Elmer Life Sciences, MA). Validation of the time activity curve with well counts is described in the Supplementary methods.

Comparison Between Well Counts and TAC

A regression analysis was performed to validate the estimates of radioactivity obtained using microPET imaging with those obtained using well counts. For the primary organs of interest, the slope of the linear regression (% ID/cc vs % ID/g) was 1.07 for blood measured within the heart on microPET (R2=0.92) and 0.8 for the heart tissue (R2=0.96).

Pharmacokinetics in Blood Pool

Estimates of radioactivity within the blood pool over time were fit with a biphasic clearance curve, $$C_t = Ae^{-t/\alpha} + Be^{-t/\beta} \quad (1)$$

where $C_t$ is the blood isotope concentration at time t, A and B are pre-exponential constants, and $\alpha$ and $\beta$ are first-order hybrid time constants describing the biphasic nature of the concentration-time profile.

Autoradiography

In a limited set of studies (four mice in total), after the gamma count was obtained, the heart tissue was imaged with autoradiography. The heart was affixed to a 30 mm specimen disc (Leica, Bannockburn, Ill.) using Tissue-Tek Optimum Cutting Temperature (OCT) Compound (Sakura, Torrance, Calif.). The sample was frozen using a dry ice/isopropanol bath. Once the OCT compound was solidified, the specimen disc was placed in a Leica CM 1850 cryotome chamber (Bannockburn, Ill.) for 15 minutes to uniformly equilibrate to −22° C. The tissue cutting thickness was set to 60 um, and slices were mounted onto microscope slides. Slides were then placed in 10% natural buffered formalin for approximately one minute and then briefly (10 seconds) dipped in 100% EtOH for drying. After drying, the slides were placed in an Exposure Cassette with a Phosphor screen (Amersham Biosciences, Piscataway, N.J.). The screen was exposed to the slide overnight and the resulting images were processed by an Amersham Biosciences Storm 860.

Confocal Microscopy

Fluorescently-labeled NON-, and CRPPR- (SEQ ID NO: 1) targeted liposomes were injected into mice (n=4), which were euthanized 15 minutes later. Cardiac tissue was harvested and sliced to ~1 mm in thickness. Confocal microscopy (LSM-510, Zeiss, Thornwood, N.Y.) images were recorded with excitation at 555 nm and emission at 565 nm. For the region of interest, 16 x/y images were acquired as z-stacks each separated by 15 m and the projection images were obtained.

Inhibitor Preparation and Administration

Blank liposomes: blank liposomes (DPPC:DSPE-PEG2000=98:2 (mol/mol), with diameter 100 nm) with 300 μg lipids (12 mg/kg) in 100 μl saline were injected 15 minutes before the radiolabeled targeted liposomes. Polyinosinic acid (PI): PI (P4154), purchased from Sigma-Aldrich, was dissolved in 0.9% sterile injection saline at 2 mg/ml. A small amount of sodium hydroxide solution was added to dissolve PI powder and the pH of the PI solution was adjusted to 7.4 with HCl solution. 5 μl of PI solution (~10 μg of PI, 0.4 mg/kg) was diluted with 100 μl saline and injected 1 minute before the injection of the radiolabeled targeted liposomes. Control animals received an equal volume of saline solution. Clodronate liposomes: Clodronate liposomes were prepared as in [21]. 100 μl of clodronate liposomes (~0.05 mg, 2 mg/kg) were injected 24 hours in advance of the administration of radiolabeled targeted liposomes. Control animals received an equal volume of saline solution. Free CRPPR Peptide (SEQ ID NO: 1): 700 μg of CRPPR peptides (SEQ ID NO: 1) (25 mg/kg) were injected 1 minute before the administration of radiolabeled targeted liposomes. Control animals received an equal volume of injection saline solution.

Statistical Analysis

Data were recorded as a (mean±standard deviation) for continuous data. Significant differences were assessed using a one-tailed Student's t test, with $\alpha$ of 0.05, and by linear regression analysis. All statistical analyses were performed by using software (Excel 11.0, Microsoft, Seattle, Wash.;

GraphPrism 4, Graphpad Inc., San Diego, Calif.). A p value less than 0.05 indicated a statistically significant difference.

Example 1

Liposome Diameter, Zeta Potential, Lipo-PEG-Peptide (LPP) Incorporation, and In Vitro Binding The LPP (structure shown in FIG. 1a), radiolabeled lipid ([$^{18}$F]FDP), phospholipid (DPPC), and pegylated phospholipid (DSPE-PEG2000) were combined to produce a composition (FIG. 1b, with formulations and notation detailed in FIG. 1 caption), with a polymer brush layer of 2000 molecular weight (MW) and a ligand that was either exposed (m=3 in FIG. 1a) or buried (m=1). Initial in vitro studies indicated that the formulation of CRPPR-3:DSPE-PEG2000:DPPC=6%: 6%:88% (mol/mol) ('CRPPR' disclosed as SEQ ID NO: 1) produced effective targeting, therefore this formulation was employed in in vitro studies and as the baseline formulation in in vivo studies. In vivo results with the CRPPR-3:DSPE-PEG2000:DPPC=6%:6%:88% ('CRPPR' disclosed as SEQ ID NO: 1) were compared with matched total PEG concentration (12%), LPP concentration (6%), DSPE-PEG2000 concentration (6%), or LPP:DSPE-PEG2000 ratio (1:1), while other parameters were varied (Table 1). For abbreviations in Table 1 refer to the figure legend of FIG. 1 (above). Note at a pH of 7.0, the net charge of CRPPR (SEQ ID NO: 1), CPPRR (SEQ ID NO: 2) or CRRPP (SEQ ID NO: 7) is +2, the net charge of CRRRR (SEQ ID NO: 3) is +4, while the net charge of c(RGDY(OMe)KE) (SEQ ID NO: 6) is 0.

Example 2

PET Images

Figure 2:
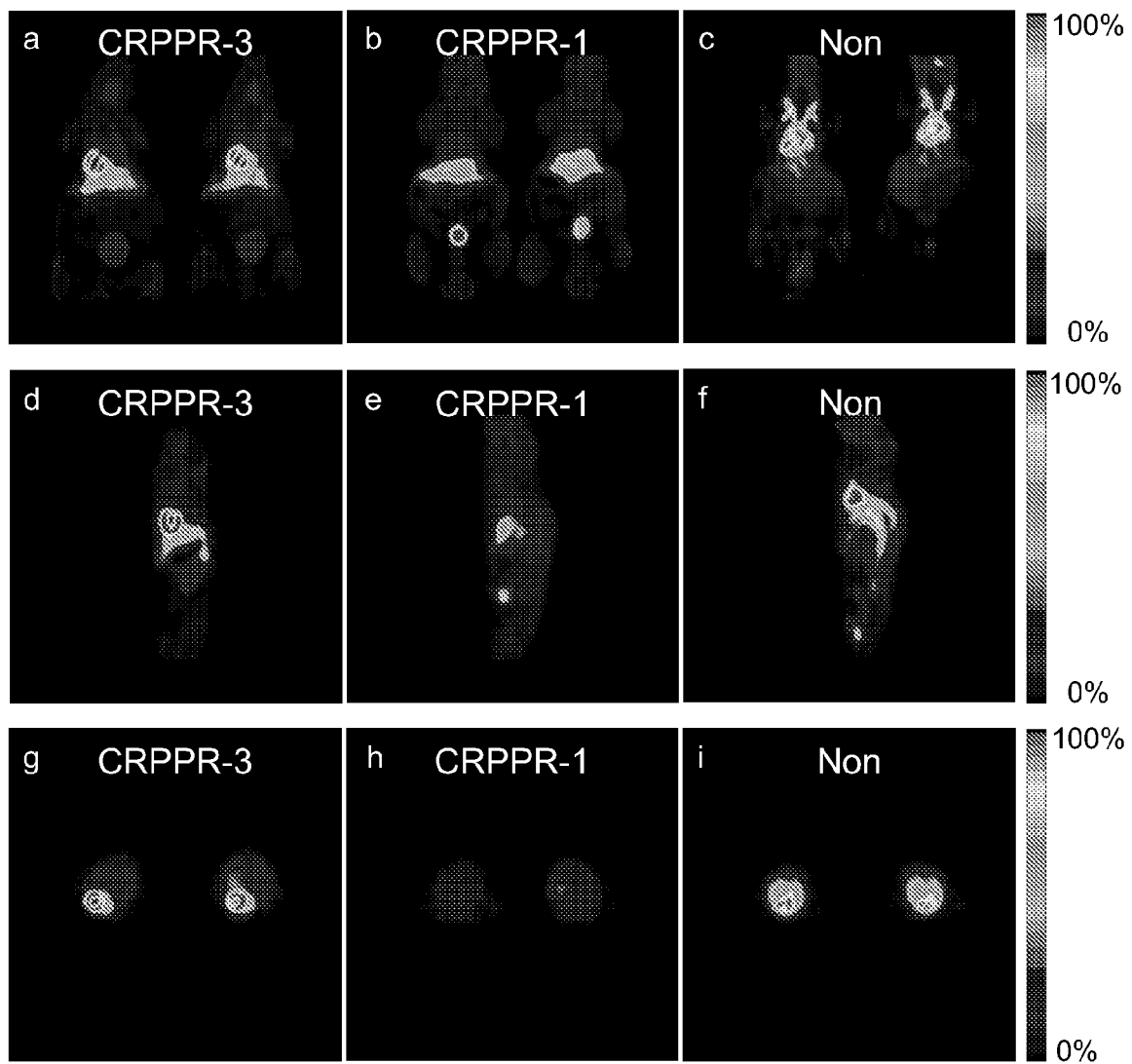
FIG. 2. (a-i) 90-minute accumulative PET images acquired after injection of radiolabeled liposomes from coronal (a-c), sagittal (d-f) and transverse views (g-i) with LPPs CRPPR-3 (a,d,g) ('CRPPR' disclosed as SEQ ID NO: 1), CRPPR-1 (b,e,h) ('CRPPR' disclosed as SEQ ID NO: 1), and NON (c,f,i).
Figure 3A:
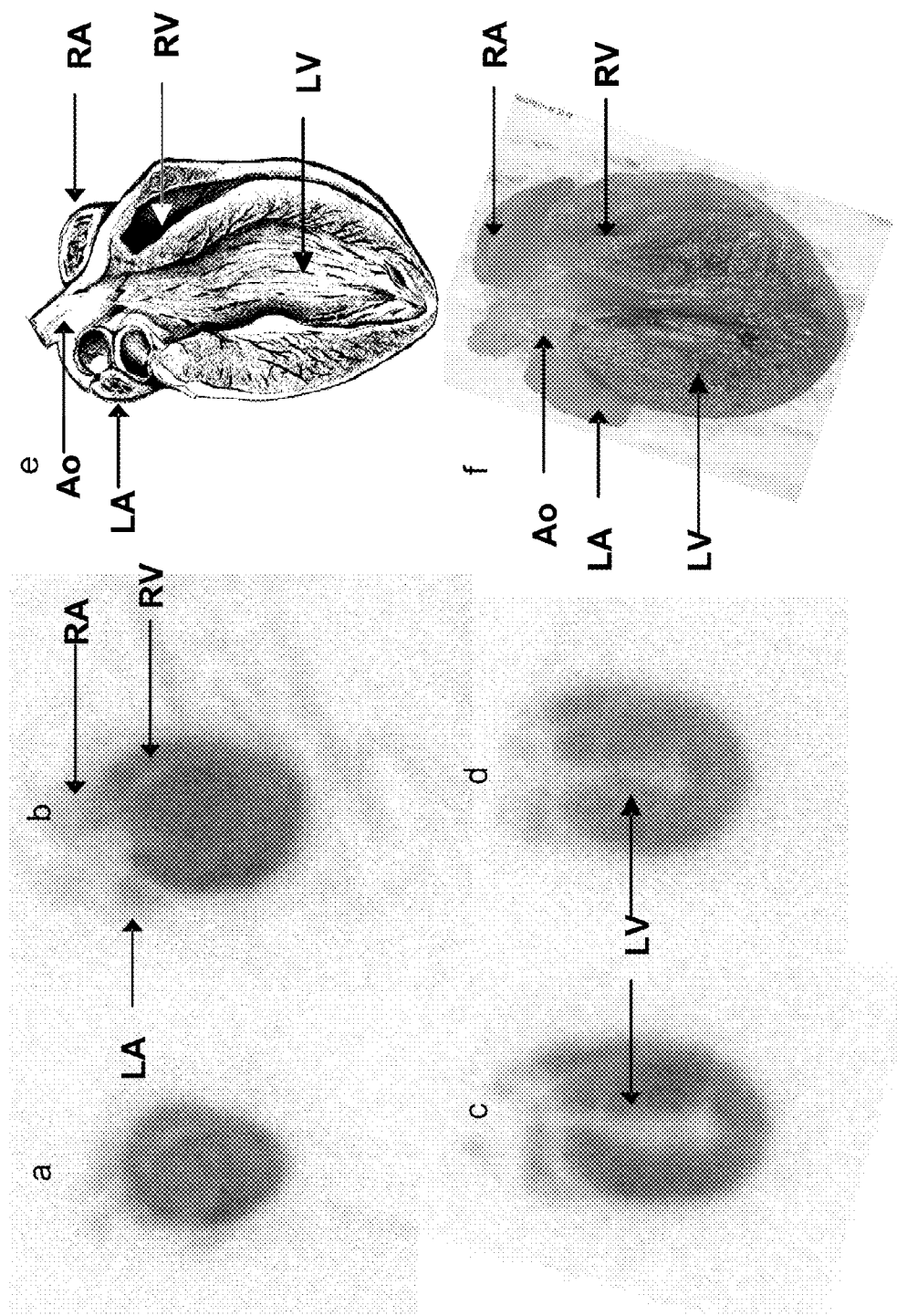
FIGS. 3A-C. High resolution autoradiography and optical imaging of the heart after injection of targeted and control compositions. (a-d) Autoradiography images acquired from 60 μm tissue slices 90 minutes after injection of CRPPR-3 liposomes ('CRPPR' disclosed as SEQ ID NO: 1). (e) Anatomic drawing of a mouse heart with the same orientation as the processed tissue slices (picture by William Moroski). (f) Digital photograph of a mouse heart fixed in 10% formalin. A for atrium, V for ventricle, L for left, R for right and Ao for aorta. (g-j) Confocal microscopy images of heart tissue after intravenous injection of CRPPR-3-('CRPPR' disclosed as SEQ ID NO: 1) (g, i), and NON- (h, j) targeted liposomes with low (g, h) and high (i, j) magnification.
Figure 3B:
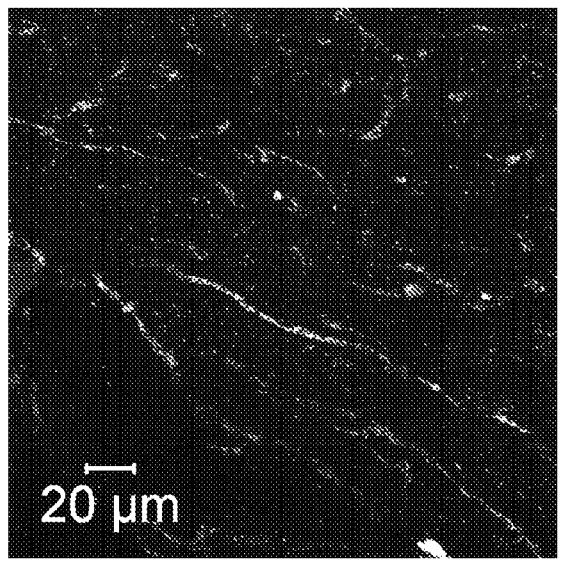
Figure 3B:
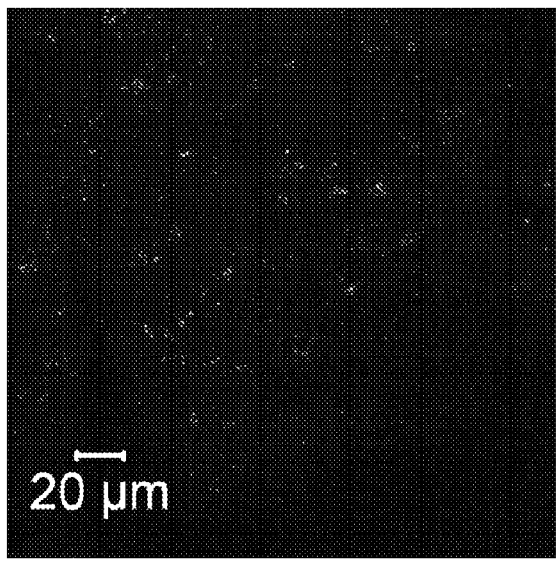
Figure 3C:
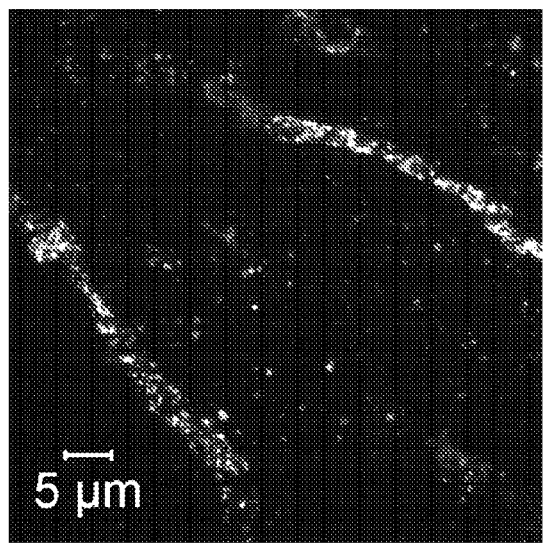
Figure 3C:
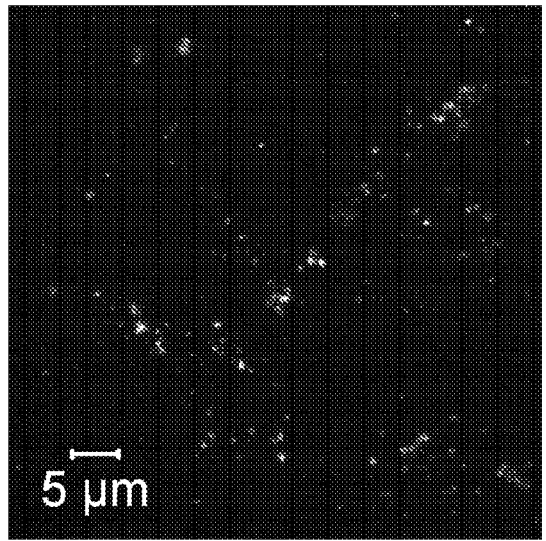

Ninety-minute accumulative PET images (FIG. 2a-i) acquired with the [$^{18}$F]FDP and CRPPR-3 ('CRPPR' disclosed as SEQ ID NO: 1) incorporated into the liposomal vectors (FIGS. 2a, d, g) demonstrate the high level of the radiotracer within the heart, a lower density within the liver, and a low concentration within the spleen and bladder. Images acquired with the shorter PEG length LPP(CRPPR-1 ('CRPPR' disclosed as SEQ ID NO: 1)) loaded onto an identical vehicle demonstrate that radioactivity has accumulated within the liver and bladder at 90 minutes and a low level of activity is present in the heart (FIGS. 2b, e, h). Clearance of the radiotracer occurs through the bladder, after metabolism in the liver separates the fatty acid chains (each with a molecular weight of 256) from the head group containing the isotope (with a molecular weight of 94). By comparison, images acquired with the identical vehicle, without a peptide attached to the liposome, demonstrate that the radioisotope is primarily circulating within the blood volume throughout the ninety-minute scan, visualized in the heart chamber and carotid vessels (FIGS. 2c, f, i).

Autoradiography confirmed that the radiotracer was present throughout the atria and both ventricles (FIG. 3 a-f), although the highest counts were observed within the thick ventricular walls. Confocal microscopy confirmed that CRPPR-targeted liposomes ('CRPPR' disclosed as SEQ ID NO: 1) bind to blood vessel walls within the heart (FIG. 3 g-j).

TABLE 1

| Liposome Formulation (mol %) | | | | Diameter (nm) | | Zeta Potential (mv) | | $\dfrac{\text{Measured}\left(\frac{\text{LPP}}{\text{DPPC}}\right)}{\text{Predicted}\left(\frac{\text{LPP}}{\text{DPPC}}\right)} \times 100$ | |
|---|---|---|---|---|---|---|---|---|---|
| LPP type | LPP | DSPE-PEG 2000 | DPPC | Mean | SD | Mean | SD | Mean | SD |
| CRPPR-3 | 6 | 6 | 88 | 110 | 38 | 31 | 9 | 135 | 30 |
| CRPPR-3 | 10 | 2 | 88 | 192 | 89 | 33 | 18 | 74 | 9 |
| CRPPR-3 | 3 | 3 | 94 | 72 | 27 | 3 | 2 | 74 | 8 |
| CRPPR-3 | 6 | 6 | 92 | 80 | 36 | −24 | 2 | 83 | 1 |
| NON | 0 | 12 | 88 | 71 | 26 | −48 | 10 | N/A | N/A |
| RGD-3 | 6 | 6 | 88 | 84 | 32 | −31 | 2 | 72 | 13 |
| CRPPR-2 | 6 | 6 | 88 | 93 | 35 | 26 | 4 | 79 | 18 |
| CRPPR-1 | 6 | 6 | 88 | 82 | 26 | 34 | 2 | 137 | 29 |
| CPPRR-3 | 6 | 6 | 88 | 138 | 11 | 42 | 3 | 120 | 7 |
| CRRPP-3 | 6 | 6 | 88 | 148 | 10 | 41 | 9 | 116 | 7 |
| CRRRR-3 | 6 | 6 | 88 | 169 | 13 | 39 | 8 | 83 | 2 |

Table 1 discloses 'CRPPR' as SEQ ID NO: 1, 'CPPRR' as SEQ ID NO: 2, 'CRRPP' as SEQ ID NO: 7 and 'CRRRR' as SEQ ID NO: 3.

Using flow cytometry (FIG. 1c), both endothelial and melanoma cells incubated in culture with calcein-containing compositions targeted by CRPPR-3 ('CRPPR' disclosed as SEQ ID NO: 1) or CPPRR-3 ('CPPRR' disclosed as SEQ ID NO: 2) showed a significantly higher fluorescence intensity than cells incubated with compositions without the lipopeptide (p<0.05). Endothelial cells incubated with compositions containing CRRPP-3 ('CRRPP' disclosed as SEQ ID NO: 7) demonstrated a lower fluorescence intensity than those incubated with compositions containing CRPPR-3 ('CRPPR' disclosed as SEQ ID NO: 1) or CPPRR-3 ('CPPRR' disclosed as SEQ ID NO: 2).

Example 3

Figure 4A:
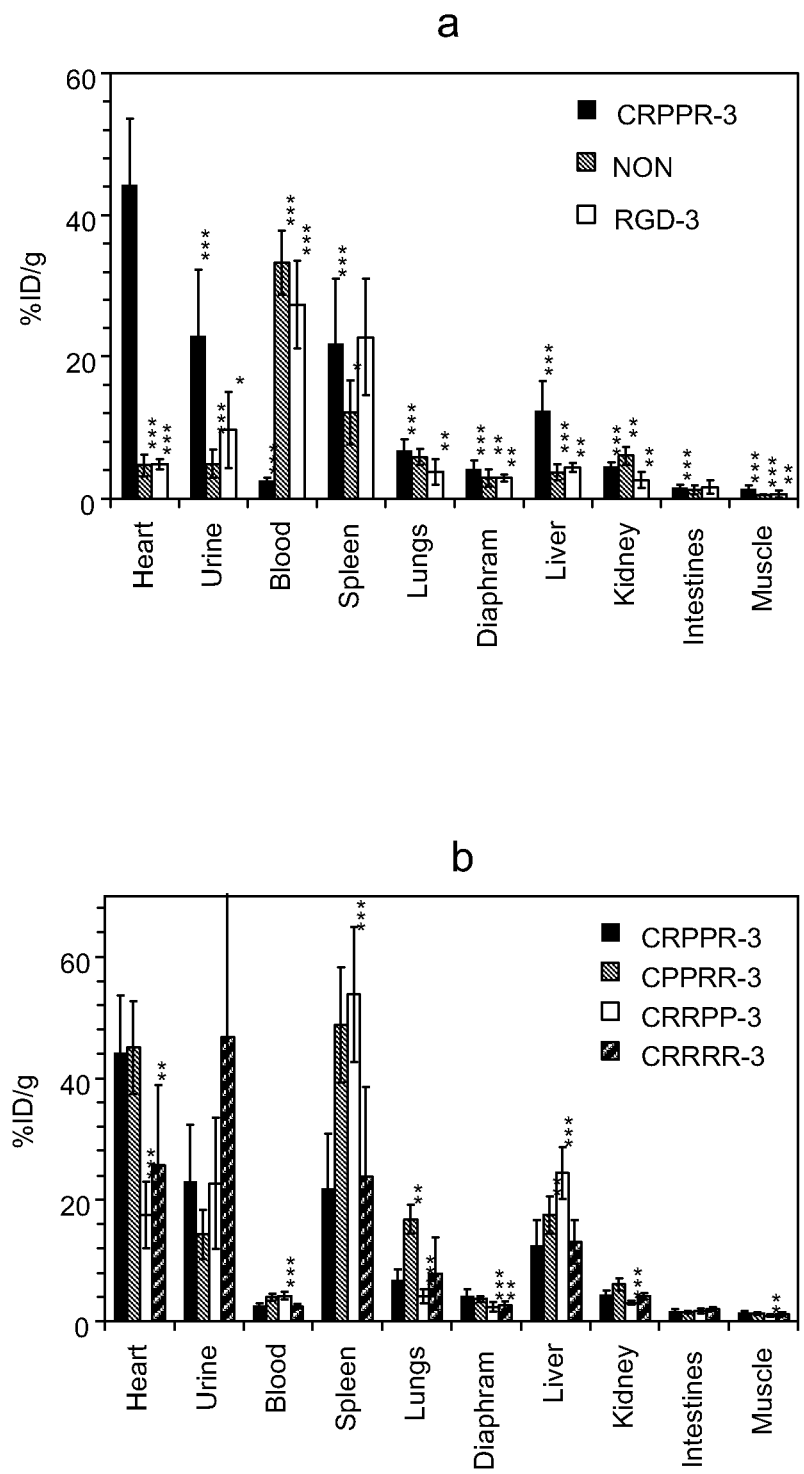
FIG. 4A discloses 'CRPPR' as SEQ ID NO: 1, 'CPPRR' as SEQ ID NO: 2, 'CRRPP' as SEQ ID NO: 7 and 'CRRRR' as SEQ ID NO: 3.
Figure 4B:
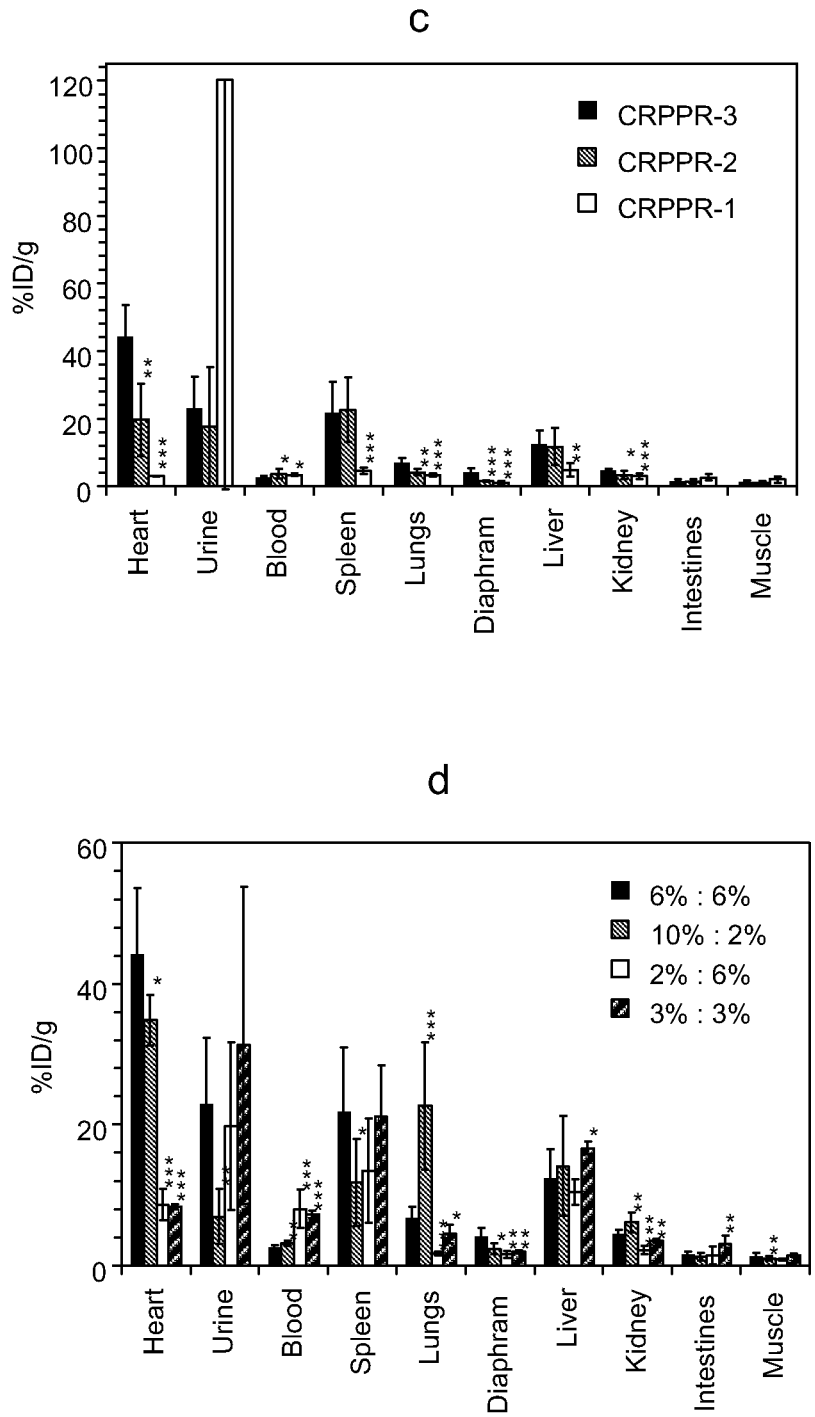
FIG. 4B discloses 'CRPPR' as SEQ ID NO: 1.

Effect of Peptide and Surface Architechture on Biodistribution at 90 Minutes Well counts obtained from harvested tissues at the ninety-minute time point quantify the differences in biodistribution produced by the peptide (FIGS. 4a and b), the length of the PEG spacer between the fatty acid and CRPPR peptide (SEQ ID NO: 1) portions of the LPP (FIG. 4c), and the molar fraction of the CRPPR-3 ('CRPPR' disclosed as SEQ ID NO: 1) incorporated within the vehicle (FIG. 4d). When injected on a vehicle containing CRPPR-3 ('CRPPR' disclosed as SEQ ID NO: 1), the concentration of the tracer was significantly higher within the heart than other organs (p<0.001), with a target to skeletal muscle ratio as high as 100 in individual animals (averaging 32) and a mean heart concentration of 44±9% injected dose per gram of tissue (ID/g). For CRPPR-3 ('CRPPR' disclosed as SEQ ID NO: 1), activity within the liver and spleen was significantly lower than the heart at 22±9 and 12±4% ID/g (p<0.001). Other arginine-rich peptidyl liposomes bound to the heart (FIG. 4b) at levels of 39±13, 26±13, 17±5% ID/g for CPPRR-3 ('CPPRR' disclosed as SEQ ID NO: 2), CRRRR-3 ('CRRRR' disclosed as SEQ ID NO: 3), and CRRPP-3 ('CRRPP' disclosed as SEQ ID NO: 7), respectively, with target to skeletal muscle ratios of 32, 23 and 19. Injection of vehicles with the cyclized RGD peptide and an otherwise identical liposome surface architecture did not produce radioactivity above the baseline (no-peptide) case. The cyclized RGD and no-peptide controls also resulted in significantly lower activity levels within the liver and urine at 90 minutes as compared with arginine-rich peptidyl vehicles (p<0.05).

When the PEG spacer length supporting the peptide was decreased from 3600 to 1200 MW within a surrounding brush layer of DSPE-PEG2000, such that the peptide was shielded by the brush layer, binding of the isotope-containing particle decreased ~10 fold (FIG. 4c). For compositions targeted with CRPPR-1 ('CRPPR' disclosed as SEQ ID NO: 1), the isotope concentration within the urine at 90 minutes was greatly increased (p<0.01), demonstrating the rapid clearance of the tracer. For compositions targeted with CRPPR-2 ('CRPPR' disclosed as SEQ ID NO: 1), isotope accumulation within the heart was in all cases less than compositions containing CRPPR-3 (p<0.05) ('CRPPR' disclosed as SEQ ID NO: 1), and greater than compositions containing CRPPR-1 (p<0.001) ('CRPPR' disclosed as SEQ ID NO: 1).

Radioactivity detected within the heart increased with increasing CRPPR-3 ('CRPPR' disclosed as SEQ ID NO: 1) content from 2 to 6%, with the molar percent of DSPE-PEG2000 held constant at 6% (p<0.001, FIG. 4d). Neither LPP incorporation or resulting radioactivity increased further as the CRPPR-3 ('CRPPR' disclosed as SEQ ID NO: 1) content was increased to 10% (with 2% DSPE-PEG2000), although we note that the 10% CRPPR-3 ('CRPPR' disclosed as SEQ ID NO: 1) compositions were difficult to extrude and had a higher mean diameter of 192±89 nm (Table 1). For compositions with 2% CRPPR-3 ('CRPPR' disclosed as SEQ ID NO: 1), increasing the molar percentage of DSPE-PEG2000 from 6 to 10% increased the percentage circulating within the blood (p<0.001) at 90 minutes but further decreased the activity within the heart (p<0.01) (data not shown).

Example 4

Real-Time Pharmacokinetics

Figure 5A:
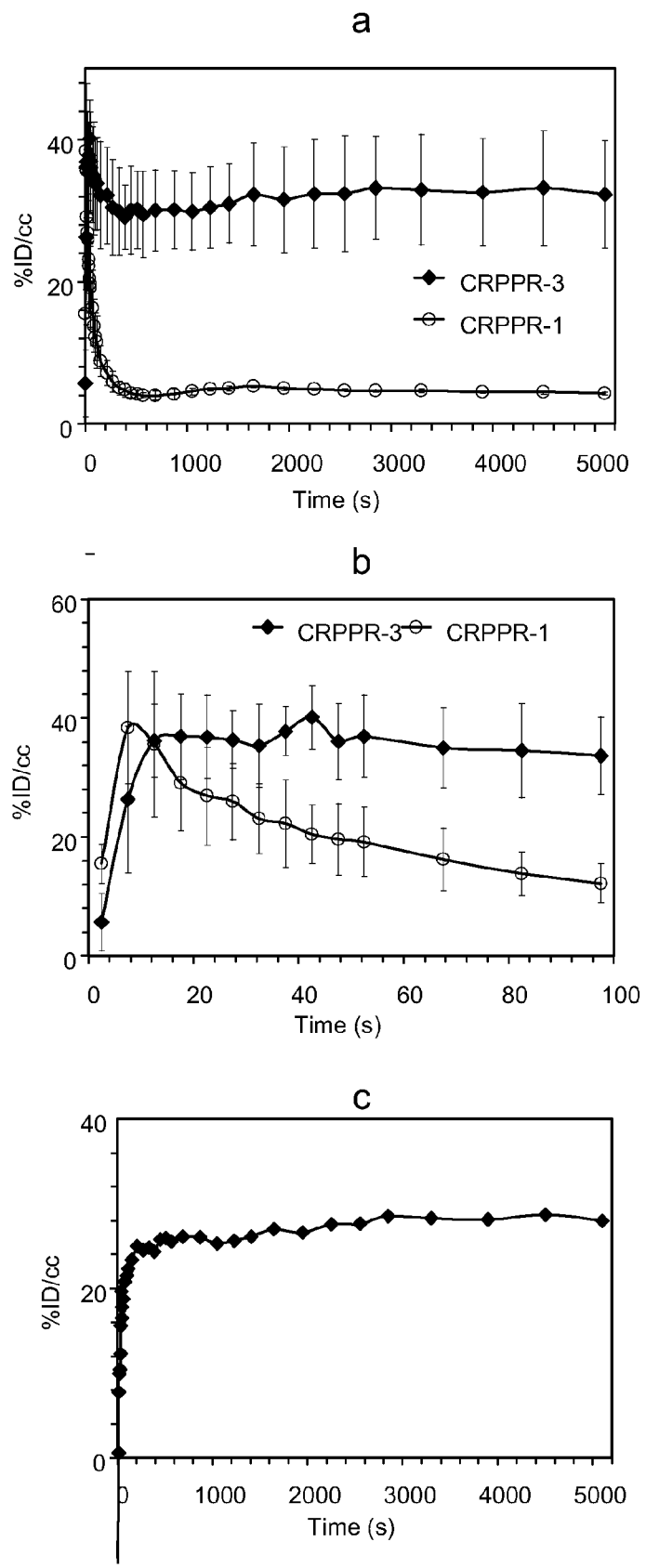
FIGS. 5A-C. Time activity curves (TACs) and Logan Plot from dynamic PET analysis of various LPP liposomes. (a)-(b) TACs for heart muscle, (c) difference between CRPPR-3 ('CRPPR' disclosed as SEQ ID NO: 1) and CRPPR-1 liposomes ('CRPPR' disclosed as SEQ ID NO: 1) in TAC from heart muscle. Subtraction of non-binding CRPPR-1 ('CRPPR' disclosed as SEQ ID NO: 1) compositions removes the effect of the blood pool, showing accumulation of compositions within heart muscle. (d) results of Logan analysis for 4 injections of CRPPR-3 liposomes ('CRPPR' disclosed as SEQ ID NO: 1), plotting the time integral of activity at target, $C_t(t)$ against the integral of activity in blood, $C_p(t)$, each normalized by $C_t(t)$. (e) summary of slope and intercept for plots as shown in (d). The higher volume of distribution of CRPPR-3 ('CRPPR' disclosed as SEQ ID NO: 1) compositions indicates higher avidity. (f-i) TACs for regions of interest. (f) blood within the heart chamber, (g) liver, (h) spleen, and (i) bladder.
Figure 5B:
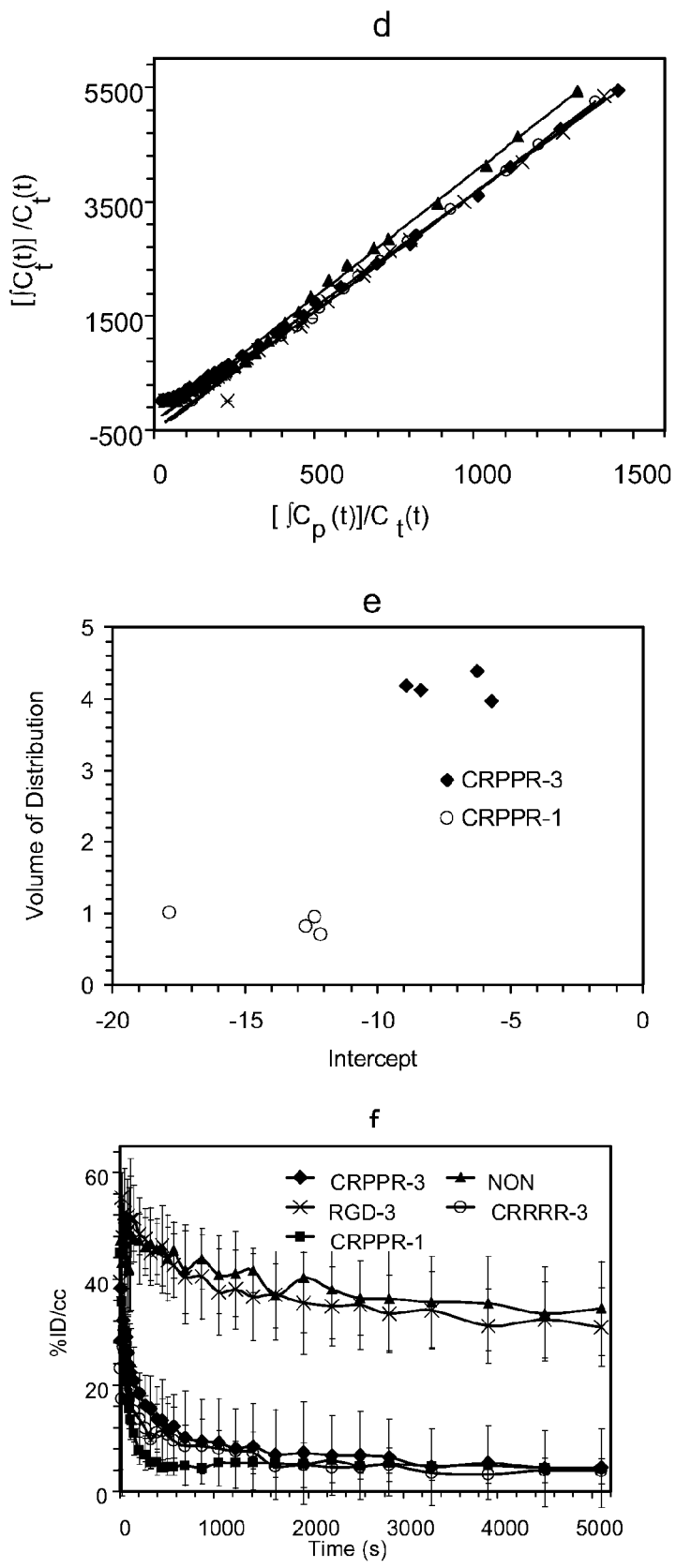
Figure 5C:
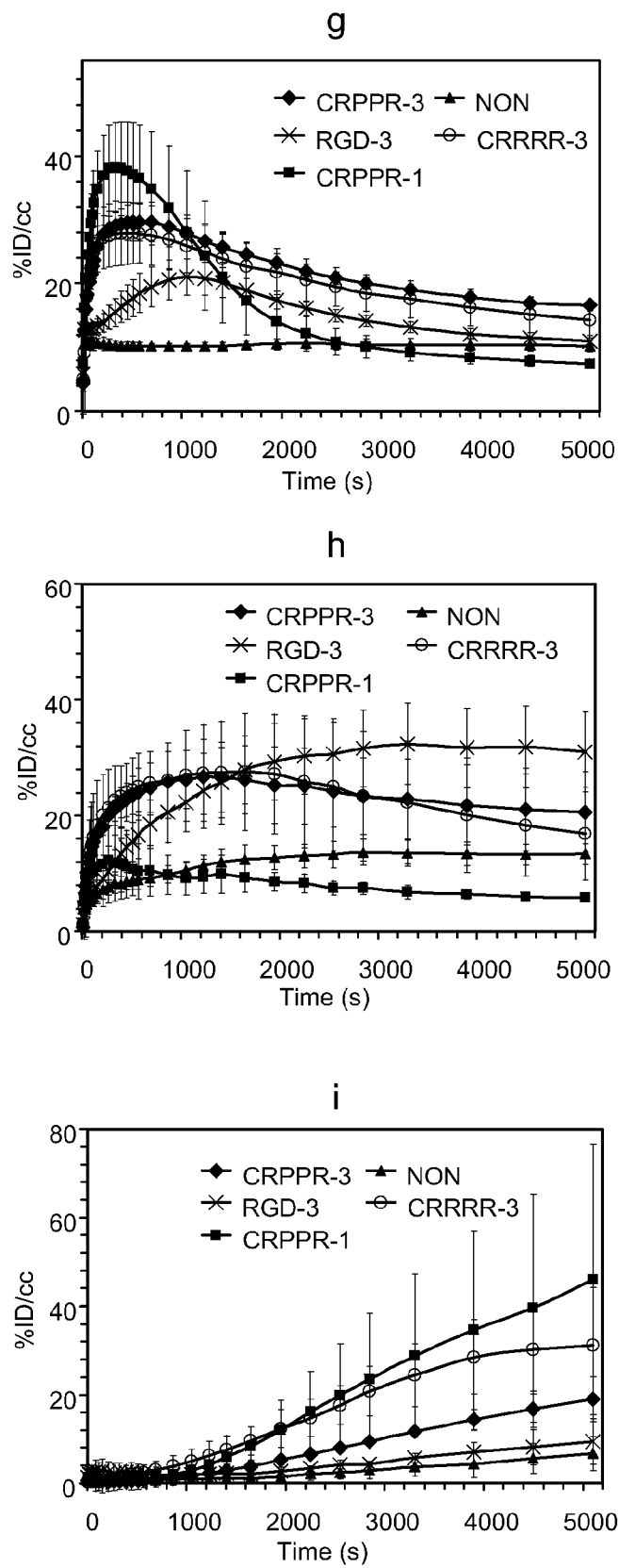

Dynamic PET analysis provides the opportunity to evaluate the rate of accumulation of the isotope at the target site and to detect accumulation in unexpected targets in real time (Supplemental Video 1 and 2). Accumulation of radiolabeled-compositions containing CRPPR-3 ('CRPPR' disclosed as SEQ ID NO: 1) was very rapid (tens of seconds) within the heart (FIG. 5a-b). Compositions containing CRPPR-1 ('CRPPR' disclosed as SEQ ID NO: 1) cleared rapidly from the heart, with activity significantly below CRPPR-3 ('CRPPR' disclosed as SEQ ID NO: 1) from 40 seconds after the start of the injection (FIG. 5b) (p<0.01). Since the heart region of interest (ROI) evaluated with microPET also includes circulating blood within the heart, the heart TAC resulting from the injection of compositions containing CRPPR-1 ('CRPPR' disclosed as SEQ ID NO: 1) (which did not bind but had similar blood pharmacokinetics to CRPPR-3 ('CRPPR' disclosed as SEQ ID NO: 1)) was subtracted from the CRPPR-3 ('CRPPR' disclosed as SEQ ID NO: 1) TAC. The resulting plot (FIG. 5c) indicates that the bound activity within the heart increases rapidly over an interval less than 100 seconds, and continues to increase at a slower rate over the duration of the scan. When fit to a single exponential, a time constant of ~30 seconds for accumulation of activity for particles containing CRPPR-3 ('CRPPR' disclosed as SEQ ID NO: 1) was estimated based on FIG. 5c.

The volume of distribution of different tracers in the myocardium was calculated using a Logan plot [28]. The volume of distribution of particles containing CRPPR-3 ('CRPPR' disclosed as SEQ ID NO: 1) (for example FIG. 5d) is significantly larger than CRPPR-1 ('CRPPR' disclosed as SEQ ID NO: 1) (FIG. 5e) (p<0.001), indicating higher binding avidity. Note that the estimated values are conservative, particularly for CRPPR-3 ('CRPPR' disclosed as SEQ ID NO: 1), as the effects of possible metabolites in blood and the contribution of the blood activity in the myocardial region were not accounted for. Following correction for circulating metabolites, the true volume of distribution of compositions containing CRPPR-3 ('CRPPR' disclosed as SEQ ID NO: 1) can be significantly greater than four.

TABLE 2

| | Blood Clearance | | | | Heart Muscle | | Liver | | Spleen | |
|---|---|---|---|---|---|---|---|---|---|---|
| | A | | B | | Peak time | Peak value | Peak time | Peak value | Peak time | Peak value |
| LPP type | (% ID/cc) | α (sec) | (% ID/cc) | β (sec) | (sec) | (% ID/cc) | (sec) | (% ID/cc) | (sec) | (% ID/cc) |
| CRPPR-3 | 24 | 194 | 11 | 4724 | 23 | 39 | 570 | 30 | 1230 | 27 |
| NON | 46 | 9653 | 0.45 | −1835 | N/A | N/A | N/A | 11 | N/A | 10 |
| RGD-3 | 17 | 996 | 34 | 57537 | N/A | N/A | 1050 | 21 | 3300 | 32 |
| CPPRR-3 | 21 | 160 | 16 | 5977 | 23 | 44 | 570 | 28 | 2850 | 30 |
| CRRPP-3 | 25 | 110 | 13 | 8410 | 23 | 33 | 510 | 33 | 2850 | 38 |
| CRRRR-3 | 17 | 216 | 9 | 4202 | 53 | 38 | 510 | 28 | 1650 | 28 |
| CRPPR-1 | 44 | 66 | 5.3 | 32383 | 8 | 30 | 330 | 38 | 270 | 12 |

Table 2 discloses 'CRPPR' as SEQ ID NO: 1, 'CPPRR' as SEQ ID NO: 2, 'CRRPP' as SEQ ID NO: 7, and 'CRRRR' as SEQ ID NO: 3.

Gross differences between PET images were visible in the blood clearance rate of compositions depending on the attached peptide (FIG. 5f). Estimates of radioactivity within the blood pool over time were fit with a biphasic clearance curve (1), with the constants as shown in Table 2. Table 2 shows circulation time constants for [$^{18}$F] in the blood pool and peak concentrations and accumulation time constants for organs as assessed from PET TACs. Without an LPP and with 12% DSPE-PEG2000 (NON in Table 2), the particle was long circulating, with an $\alpha$ value of $10^4$ seconds. Without an LPP and with 6% DSPE-PEG2000, the particle is similarly long circulating (data not shown). Compositions coated with RGD-3 were long circulating as indicated by $\alpha$ and $\beta$ values of $10^3$ and $10^5$ seconds, respectively. The presence of CRPPR (SEQ ID NO: 1), CPPRR (SEQ ID NO: 2), CRRPP (SEQ ID NO: 7), or CRRRR (SEQ ID NO: 3) on the liposome substantially reduced the circulation time (even with the peptide shielded by a longer brush layer) with $\alpha$ values of $\sim 10^2$ seconds.

Example 5

RES Recognition and Clearance

For compositions containing the arginine-rich linear peptide, accumulation in the liver is very rapid (570 seconds or less in all cases) (FIGS. 5g, h, i and Table 2). Alternatively, compositions containing RGD-3 reach a greater peak concentration within the spleen as compared with the liver (p<0.05), with the peaks observed at 3300 and 1050 seconds for spleen and liver, respectively.

With CRPPR-1-targeted compositions ('CRPPR' disclosed as SEQ ID NO: 1), clearance of the radioisotope from the liver (and accumulation in the bladder) was more rapid than observed with the longer PEG spacer (CRPPR-3 ('CRPPR' disclosed as SEQ ID NO: 1)). Compositions targeted with CRRRR-3 ('CRRRR' disclosed as SEQ ID NO: 3) also accumulated more rapidly in the bladder than CRPPR-3 ('CRPPR' disclosed as SEQ ID NO: 1) (FIG. 5i).

For compositions containing RGD-3, the concentration within liver, spleen and bladder (FIG. 5g-i) indicate that a fraction was metabolized through the liver (concentration peaking at 1050 seconds) and cleared through the urine. At the 90 minute time point, accumulation of activity within the liver was not significantly different than the no-peptide control (p=0.17).

Example 6

RES Inhibitors

In order to increase the accumulation at the target site, several methods for the reduction of liver and spleen uptake were evaluated, including the pre-administration of polyinosinic acid, blank liposomes, clodronate liposomes, or free CRPPR peptide (SEQ ID NO: 1). Pre-administration of 12 milligram per kilogram of body weight (mg/kg) of blank liposomes did not significantly change the biodistribution of the targeted liposomes (p=0.10, data not shown).

Figure 6A:
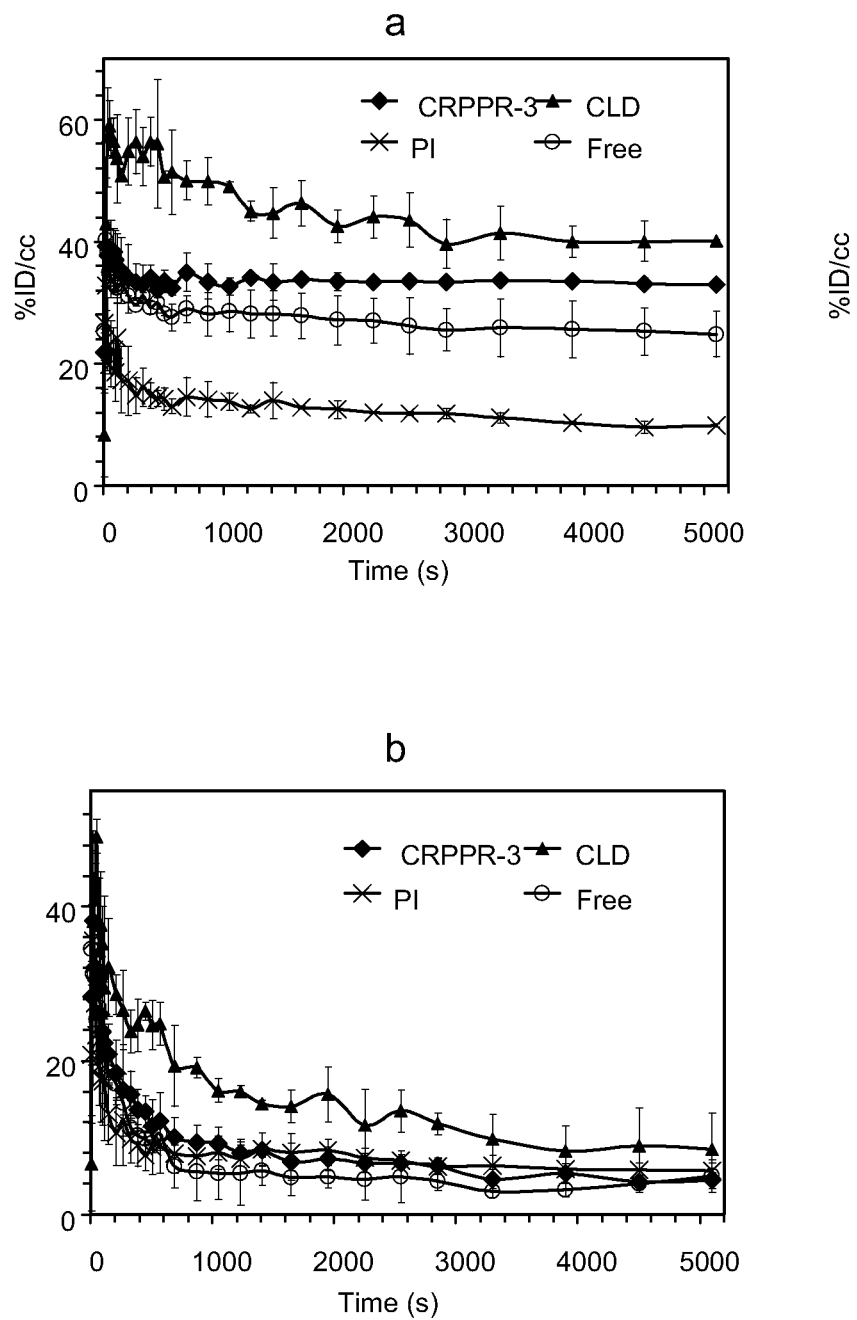
FIGS. 6A-B. TACs from dynamic PET analysis for (a) heart muscle (b) blood pool (c) liver (d) spleen (e) bladder after injection of CRPPR-3 ('CRPPR' disclosed as SEQ ID NO: 1) liposomes and various inhibitors. Abbreviations: CRPPR-3 ('CRPPR' disclosed as SEQ ID NO: 1): no inhibitors; CLD: clodronate liposomes injected 24 hours in advance; PI: poly(inosinic acid) injected 1 minute in advance; Free: free CRPPR peptide (SEQ ID NO: 1) injected 1 minute in advance of CRPPR-3 liposome ('CRPPR' disclosed as SEQ ID NO: 1) injection. Well counts at 90 minutes after injection: the ratios of radioactivity in the heart with and without inhibitors are 1.30, 0.59 and 0.81 for CLD, PI and Free, p=0.10, <0.01, and <0.05, respectively.
Figure 6B:
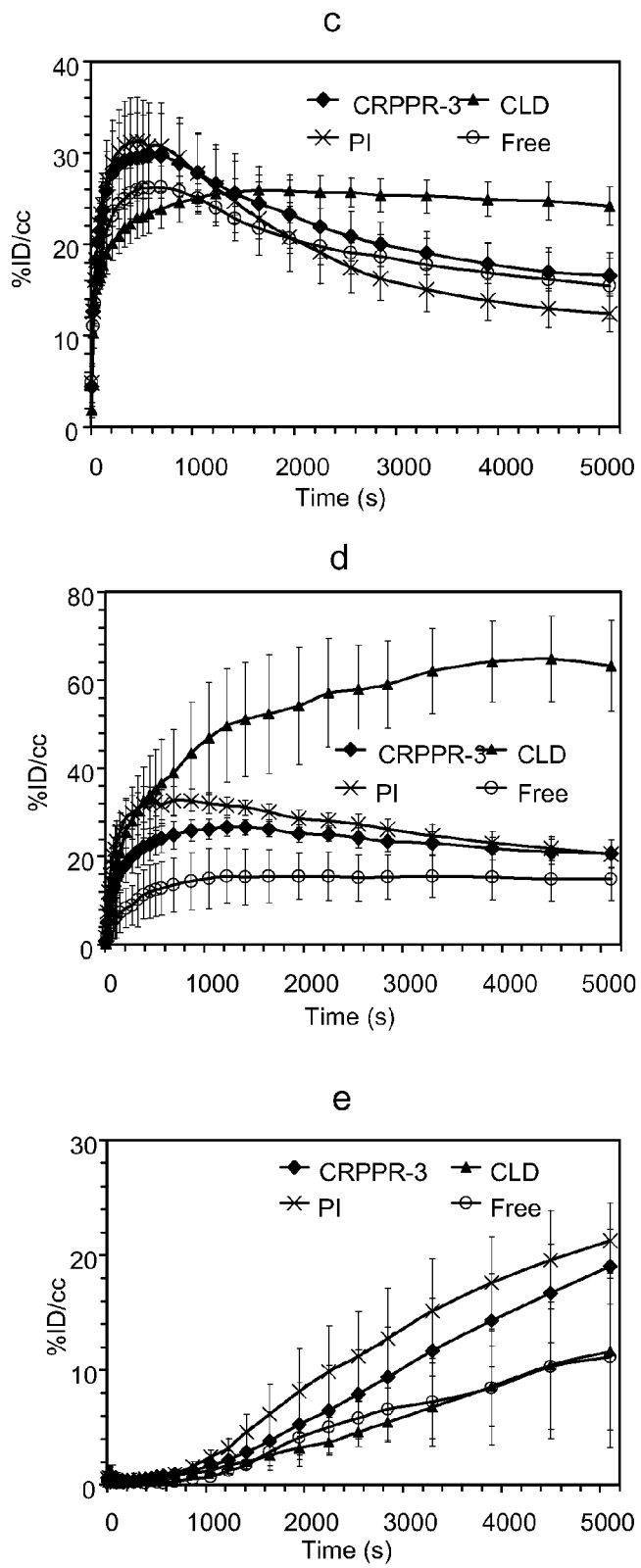

When clodronate liposomes were administered 24 hours before compositions containing CRPPR-3 ('CRPPR' disclosed as SEQ ID NO: 1), the circulation time of the compositions and binding of the compositions to the heart increased at the early time points (before 500 sec), each as compared with matched controls not receiving clodronate (p<0.001, FIG. 6a-b). However, radioactivity in the heart decreased by 10% over the 90-minute scan (not observed in the absence of clodronate), and activity simultaneously increased within the spleen (FIGS. 6a, d). Early liver uptake (before 1000 seconds) was significantly lower than observed without clodronate (p<0.05) (FIG. 6c). Liver activity does not decrease over the scan (ending higher than without clodronate) (FIG. 6c), indicating that the probe is not metabolized and cleared, and the accumulation of activity within the urine at the 90-minute time point was significantly decreased (p<0.05) (data not shown).

Pre-administration of polyinosinic acid (0.4 mg/kg) decreased accumulation within the heart by 41% at the 90 minute time point (p<0.05), and this decrease was significant from the six-minute time point forward (p<0.01, FIG. 6a). Pre-administration of the free CRPPR peptide (SEQ ID NO: 1) (25 mg/kg) decreased the accumulation within the heart (p<0.05, FIG. 6a) by ~19% at the 90 minute time point (p<0.05), showing the specificity of the targeting.

Example 7

Results of Dynamic Imaging of Arginine-Rich Vehicles

Compositions targeted with short linear peptides (CRPPR (SEQ ID NO: 1) and CPPRR (SEQ ID NO: 2)) rapidly and efficiently bound to blood vessel walls in the heart at a significantly higher level than control compositions (targeted with CRRPP (SEQ ID NO: 7), CRRRR (SEQ ID NO: 3), c(RGDY(OMe)KE) (SEQ ID NO: 6) or without a peptide), showing the potential to carry a substantial payload to heart vessels. Accumulation of CRPPR-targeted compositions ('CRPPR' disclosed as SEQ ID NO: 1) within the target region increased rapidly over the first 100 seconds after injection (averaging 44% ID/g), reaching a target-to-muscle ratio of 32. Attachment of the CRPPR peptide (SEQ ID NO: 1) to a lipid composition decreased the organ specificity of targeting as compared with the phage targeting of CRPPR (SEQ ID NO: 1) described in [4], where the target-to-muscle ratio was greater than 300 fold.

Comparing both in vitro endothelial cell binding and the in vivo target-to-muscle ratio assessed by PET (~32 fold), targeting of compositions using CRPPR (SEQ ID NO: 1) and CPPRR (SEQ ID NO: 2) was similar. Alternatively, for CRRPP-targeted compositions ('CRRPP' disclosed SEQ ID NO: 7) with an identical charge but without the final arginine amino acid, in vitro binding was reduced, the target to muscle ratio decreased to ~20 fold, and RES uptake was increased (as compared with CRPPR (SEQ ID NO: 1)). Finally, CRRRR-targeted compositions ('CRRRR' disclosed as SEQ ID NO: 3) with a greater positive charge and larger number of arginine amino acids also accumulated in the heart at a lower concentration than CRPPR (SEQ ID NO: 1) but at a greater rate than the no-peptide control. Preadministration of the free CRPPR peptide (SEQ ID NO: 1) did significantly decrease in vivo binding of the CRPPR-targeted compositions ('CRPPR' disclosed as SEQ ID NO: 1), typically indicating specificity.

Dynamic imaging has great promise for effective optimization of nanoparticle drug delivery systems; and this is important due to the vast parameter space of materials, vehicle diameter, charge, surface architecture, ligands, molecular targets and release mechanisms for the dissociation of the vehicle and drug. While imaging has played a role, quantitative measurement of the pharmacokinetics with dynamic imaging has thus far been limited. In this study, dynamic PET facilitated the evaluation of the circulation, targeting, and metabolism of the lipid composition.

The literature on the pharmacokinetics of peptide-targeted particles includes contradictory reports as to whether the presence of a peptide on the surface substantially reduces the circulation lifetime of the composition [29]. Here, compositions with a charged linear peptide (CRPPR (SEQ ID NO: 1), CPPRR (SEQ ID NO: 2), CRRRR (SEQ ID NO: 3) or CRRPP (SEQ ID NO: 7)) on the surface were cleared very rapidly.

Alternatively, compositions with a neutrally-charged cyclized RGD peptide circulate far longer than the imaging interval.

A comparison of the volume distribution of compositions demonstrated that the compositions accumulate at the target site at a rate that is proportional to their availability within the blood. Uptake within the heart appears to be limited by the rapid uptake within the liver, as the ratio of target on to off rate remains constant over time. Depletion of macrophages prior to injection of the compositions increased circulation lifetime and targeted accumulation at the early time points. Preadministration of polyinosinic acid (a scavenger receptor competitor) significantly decreased accumulation within the heart but also produced lesser changes in circulation and metabolism of the compositions.

The use of a radiolabeled lipid also facilitated an evaluation of targeting dynamics with differing composition surface architecture. The accumulation in the heart of targeted liposomes with the CRPPR peptide (SEQ ID NO: 1) supported on a PEG-spacer of 3600 molecular weight (MW) was ~10 times higher than compositions with a PEG-spacer of 1200 MW (the surrounding PEG brush of the liposome was 2000 MW). The presence of a brush layer, extending beyond the targeting ligand, blocked adhesion of the compositions to the target, but did not block uptake and rapid metabolism by the liver. The presence of a high peptide concentration (6 mol % or approximately ~6000 peptide groups per liposome) was important to maximize local uptake of the composition. Increased targeting with a dense peptide coating is consistent with previous studies in which antibodies were targeted to the endothelium of the lung [8].

Dynamic PET analysis of [$^{18}$F]FDP was also used to measure the clearance of this radiolabeled lipid from the liver, as excretion of the $^{18}$F label requires cleavage of the fatty acids. With the exception of studies involving CRRRR (SEQ ID NO: 3), in all data reported here and in [25], activity in the bladder increased only after a delay of ~1000 seconds. With compositions containing CRRRR (SEQ ID NO: 3), activity in the bladder increased immediately after injection of the compositions. The presence of large numbers of arginine amino acids has otherwise been reported to facilitate internalization [10]. Also, a shorter PEG spacer (CRPPR-1 ('CRPPR' disclosed as SEQ ID NO: 1)) facilitated rapid metabolism of the radioactive lipid.

Liposomes with a 6 molar percent coating of CRPPR (SEQ ID NO: 1) or CPPRR (SEQ ID NO: 2) lipoPEGpeptide, a PEG spacer of 3600 MW, and a PEG brush of 2000 MW bound to heart vasculature within 100 seconds. The rapid and specific targeting of liposomes to the heart using a surface coating of peptide demonstrates the utility of this method in drug and gene delivery applications.

Example 8

Delivery of Compounds to the Brain

Figure 7:
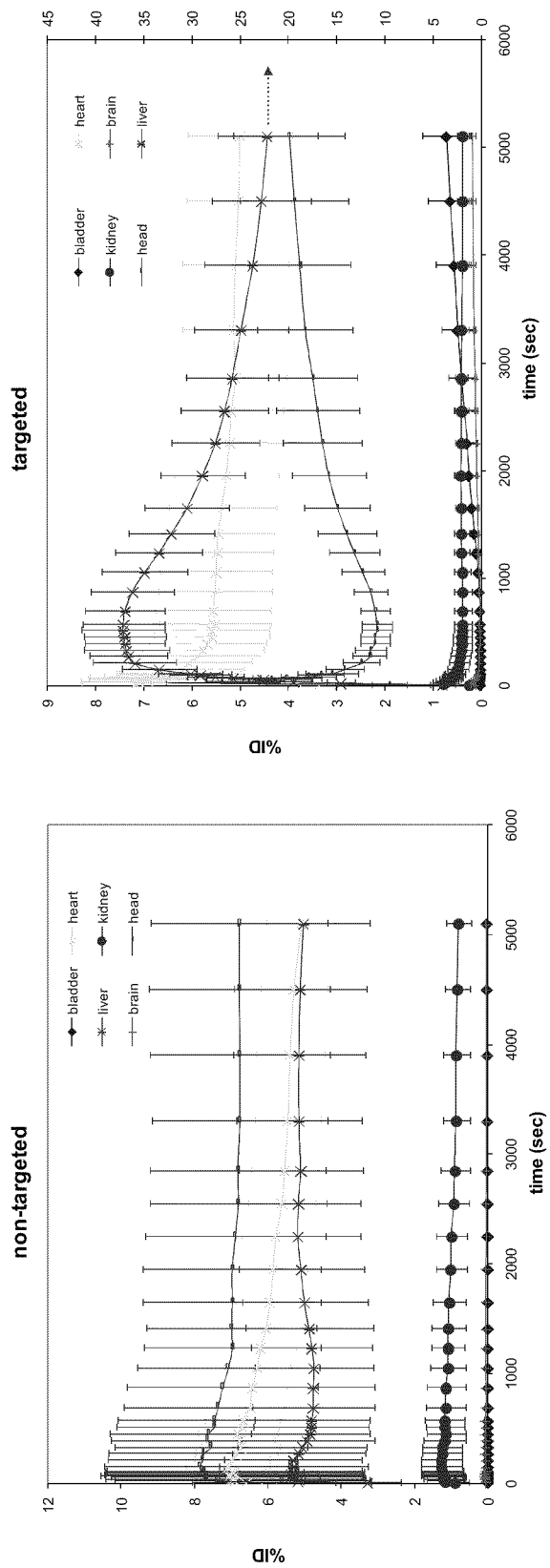
FIG. 7. TACs from dynamic PET analysis for (a) untargeted compositions and (b) peptide-targeted compositions (F18) in various organs. Biodistribution of (a) non-targeted liposomes and (b) targeted liposomes was measured as % injection dose (% ID) of the whole organs.

It was next demonstrated that the compositions of the present invention can be used to deliver a compound, e.g. a small molecule, to the brain or other organs of interest based on their metabolism in the liver. The targeted (with peptides) or untargeted (without peptides) compositions were injected into mice as described above. The particles used for the compositions were liposomes including lipids with glycerol head groups. As shown in FIG. 7(a) for injected untargeted compositions, the pharmacokinetics over 90 minutes reflect only the relative blood volume within each organ and do not demonstrate any significant specific accumulation of the compositions in the organs of the mice. As shown in FIG. 7(b) the injected targeted composition's liver uptake occurs very rapidly and the metabolism of the particle in the liver frees a small glycerol-like molecule that travels to the brain, accumulating within the brain/head region of interest (ROI) with a total percent injected dose of 4% or more.

Figure 8:
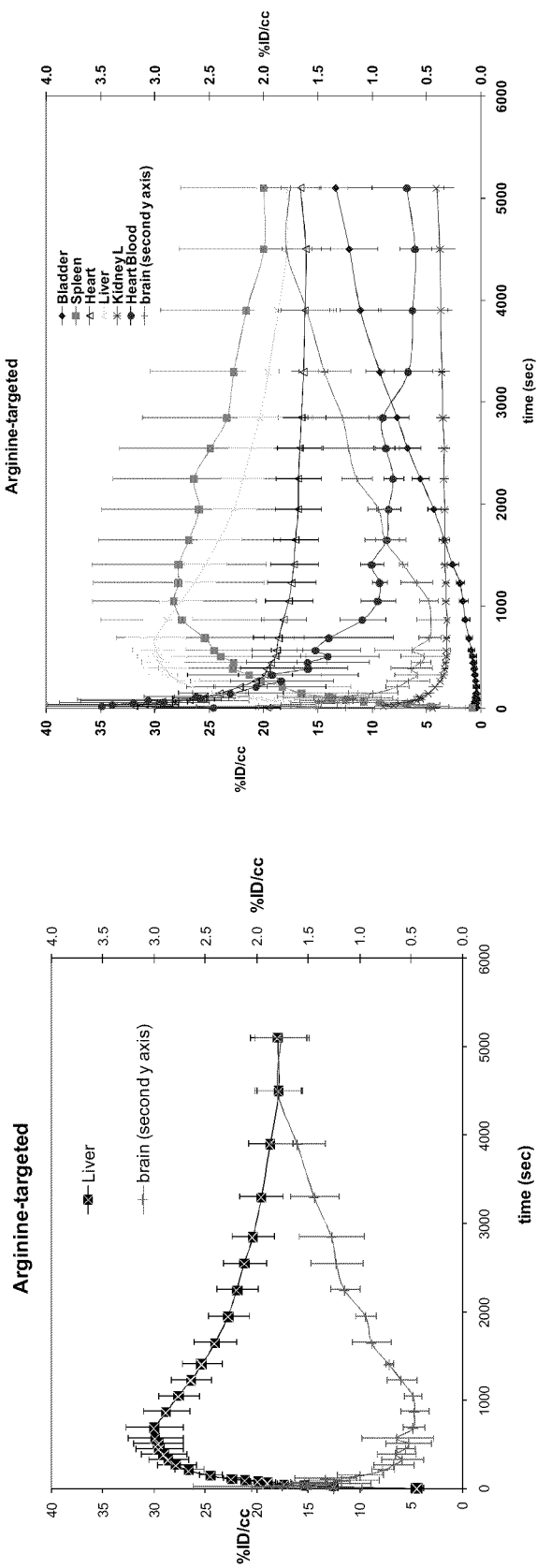
FIG. 8. TACs from dynamic PET analysis for peptide-targeted compositions. (a) Comparison of the uptake of the composition in the brain and liver that is accumulating at ~2% ID/cc over time. (b) Accumulation of composition within the brain is compared to changes in accumulation in other organs.

FIG. 8(a) shows that the uptake of the targeted compositions within the center of the cortex is a mirror (reverse) image of the liver concentration, accumulating at ~2% ID/cc over time. In addition, in FIG. 8(b) accumulation within the brain is compared to changes in other organs and shows that only the bladder (clearance) and brain activity increase over time. These data indicate that the compositions of the invention can be used to deliver compounds specifically to the brain of subjects.

Example 9

Targeting Compositions to Ischemic Hearts

Experiments were performed to demonstrate that the compositions of the invention can bind to the heart after ischemic reperfusion.

For inducing an ischemic event surgery was used to induce 1 hour of ischemia on the left heart ventricles of subject mice. Reperfusion was performed on the mice afterwards. Intravenous (i.v.) injection of the compositions was performed 24 hours later (as described in more detail below). Typically, organs were removed from the mice for analysis 90 minutes after the injection of the compositions. Animals without surgery were used as controls.

The peptides used in the composition were CRPPR (SEQ ID NO: 1) and the particles used in the composition were liposomes (DPPC: DSPE-PEG2000:LPP(CRPPR-3 ('CRPPR' disclosed as SEQ ID NO: 1))=88:6:6, mol/mol).

Figure 9:
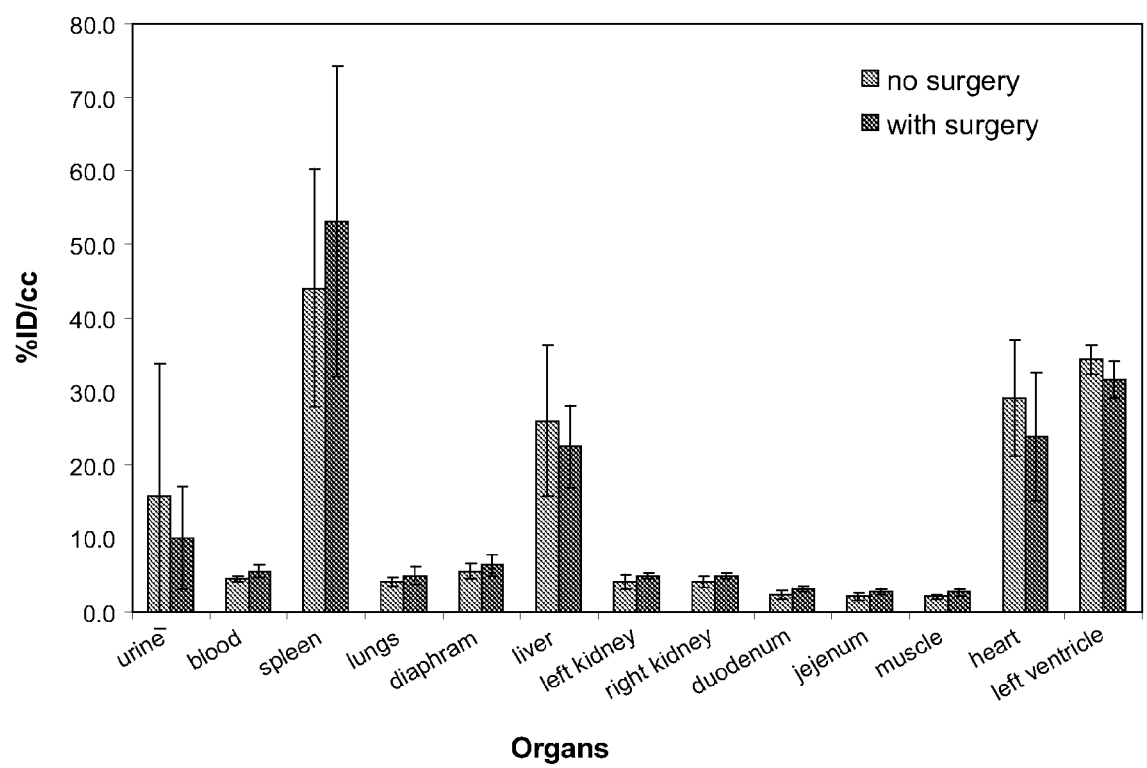
FIG. 9. Graph illustrating the calculated biodistribution of F18 in various organs after ischemia reperfusion and treatment with F-18 peptide liposome injections.
Figure 10:
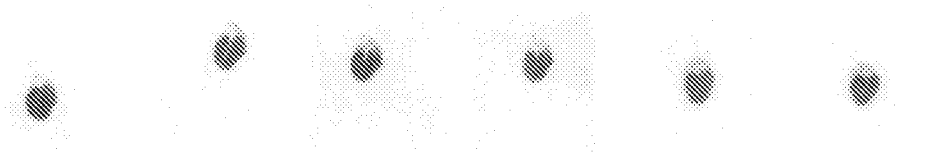
FIG. 10. Autoradiography images of hearts (both ischemic/with surgery and non-ischemic/without surgery) removed 90 minutes after F-18 peptide-liposome injections.
Figure 10:
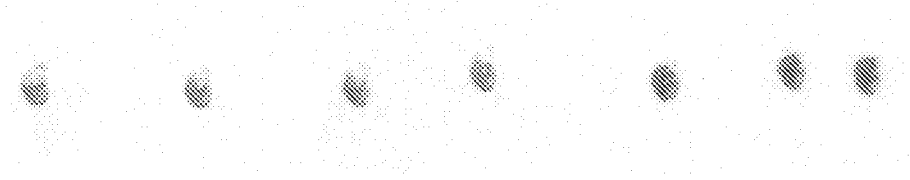

The compositions were radiolabeled with [F-18] and i.v. injected into animals. 90 min after injection of the compositions the organs were harvested; biodistribution data was calculated (FIG. 9) and autoradiography images of hearts were obtained (FIG. 10).

Figure 11:
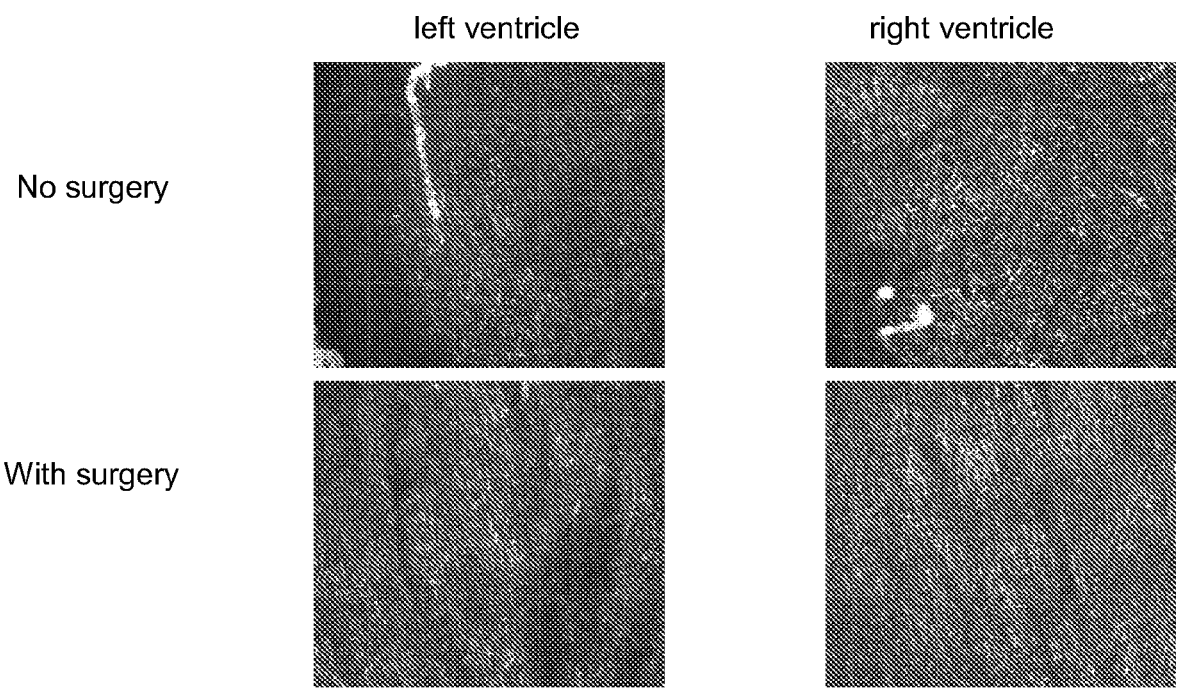
FIG. 11. Confocal micrographs of heart tissue (both ischemic/with surgery and non-ischemic/without surgery) removed 90 minutes after fluorescent dye labeled peptide-liposome injections.

Alternatively, fluorescent dyes were encapsulated into liposomes prior to injection. The compositions were i.v. injected into the animals and 15 min after the injections the hearts were harvested and confocal microscopy images were obtained (FIG. 11).

To determine whether arginine rich particles bind to the heart after ischemia reperfusion, surgery was performed resulting in 1 hour of ischemia, with reperfusion afterwards, experiments were done 24 hours after surgery. The arginine-targeted particles were labeled with 64Cu and injected systemically. Data were obtained 90 min after F-18 peptide-liposome injections; n=6 for all organs, except "left ventricle", in which n=2 (FIG. 9). The concentration of compositions within the heart was not significantly decreased at this time point.

To determine the biodistribution of the compositions after injection autoradiography was used. As in the previous figure, surgery was performed resulting in 1 hour of ischemia, with reperfusion afterwards, experiments were done 24 hours after surgery. The heart was removed 90 minutes after liposome injection. Autoradiography demonstrated that the compositions were distributed throughout the atria and ventricles with and without surgery (FIG. 10).

To further determine the biodistribution of the compositions after injection compositions labeled with fluorescent dyes were used in conjunction with optical imaging. As in the previous figures surgery was performed, resulting in 1 hour of ischemia, with reperfusion afterwards, experiments were done 24 hours after surgery. The heart was removed 90 minutes after liposome injection. Optical imaging of a probe within the center of the particle demonstrated that the intact compositions were distributed throughout the atria and ventricles with and without surgery (FIG. 11).

These data indicate that, as shown by both radiolabel and optical label experiments, the compositions of the invention can bind to the hearts of subjects after an ischemic event.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

REFERENCES CITED

1. Ding B S, Dziubla T, Shuvaev V V, Muro S, Muzykantov V R. Advanced drug delivery systems that target the vascular endothelium. Molecular Interventions 2006; 6(2):98-112.
2. Hajitou A, Pasqualini R, Arap W. Vascular targeting: Recent advances and therapeutic perspectives. Trends in Cardiovascular Medicine 2006; 16(3):80-88.
3. Ruoslahti E. Vascular zip codes in angiogenesis and metastasis. Biochem Soc Trans 2004; 32:397-402.
4. Zhang L L, Hoffman J A, Ruoslahti E. Molecular profiling of heart endothelial cells. Circulation 2005; 112(11):1601-1611.
5. Brissette R, Prendergast J K A, Goldstein N I. Identification of cancer targets and therapeutics using phage display. Curr Opin Drug Discov Dev 2006; 9(3):363-369.
6. Torchilin V P. Recent advances with liposomes as pharmaceutical carriers. Nature Reviews Drug Discovery 2005; 4(2):145-160.
7. Wilson A, Zhou W, Champion H C, Alber S, Tang Z L, Kennel S, et al. Targeted delivery of oligodeoxynucleotides to mouse lung endothelial cells in vitro and in vivo. Molecular Therapy 2005; 12(3):510-518.
8. Maruyama K, Kennel S J, Huang L. Lipid-composition is important for highly efficient target binding and retention of immunoliposomes. Proc Natl Acad Sci USA 1990; 87(15):5744-5748.
9. Wiewrodt R, Thomas A P, Cipelletti L, Christofidou-Solomidou M, Weitz D A, Feinstein S I, et al. Size-dependent intracellular immunotargeting of therapeutic cargoes into endothelial cells. Blood 2002; 99(3):912-922.
10. Patel L N, Zaro J L, Shen W C. Cell penetrating peptides: intracellular pathways and pharmaceutical perspectives Pharmaceutical Research 2007; 24(11):1977-1992.
11. Sen Gupta A, Huang G, Lestini B J, Sagnella S, Kottke-Marchant K, Marchant R E. RGD-modified liposomes targeted to activated platelets as a potential vascular drug delivery system. Thrombosis and Haemostasis 2005; 93(1):106-114.
12. Gerlag D M, Borges E, Tak P P, Ellerby H M, Bredesen D E, Pasqualini R, et al. Suppression of murine collagen-induced arthritis by targeted apoptosis of synovial neovasculature. Arthritis Research 2001; 3(6):357-361.
13. Sutcliffe-Goulden J L. The synthesis of novel $^{18}$F-labelled peptides for PET [Ph.D]. London: King's College London; 2002.
14. Raffaghello L, Pagnan G, Pastorino F, Cosimo E, Brignole C, Marimpietri D, et al. Immunoliposomal fenretinide: a novel antitumoral drug for human neuroblastoma. Cancer Lett 2003; 197(1-2):151-155.
15. Lukyanov A N, Elbayoumi T A, Chakilam A R, Torchilin V P. Tumor-targeted liposomes: doxorubicin-loaded long-circulating liposomes modified with anti-cancer antibody. Journal of Controlled Release 2004; 100(1):135-144.
16. Shadidi M, Sioud M. Selective targeting of cancer cells using synthetic peptides. Drug Resistance Updates 2003; 6(6):363-371.
17. Schiffelers R M, Koning G A, ten Hagen T L M, Fens M, Schraa A J, Janssen A, et al. Anti-tumor efficacy of tumor vasculature-targeted liposomal doxorubicin. Journal of Controlled Release 2003; 91(1-2):115-122.
18. Lestini B J, Sagnella S M, Xu Z, Shive M S, Richter N J, Jayaseharan J, et al. Surface modification of liposomes for selective cell targeting in cardiovascular drug delivery. Journal of Controlled Release 2002; 78(1-3):235-247.
19. Kamps J, Morselt H W M, Swart P J, Meijer D K F, Scherphof G L. Massive targeting of liposomes, surface-modified with anionized albumins, to hepatic endothelial cells. Proceedings of the National Academy of Sciences of the United States of America 1997; 94(21):11681-11685.
20. Simberg D, Duza T, Park J H, Essler M, Pilch J, Zhang L L, et al. Biomimetic amplification of nanoparticle homing to tumors. Proceedings of the National Academy of Sciences of the United States of America 2007; 104(3):932-936.
21. Vanrooijen N, Sanders A. Liposome-mediated depletion of macrophages-mechanism of action, preparation of liposomes and applications. Journal of Immunological Methods 1994; 174(1-2):83-93.
22. Tilcock C, Ahkong Q F, Fisher D. Tc-99m-Labeling of Lipid Vesicles Containing the Lipophilic Chelator Pe-Dtta—Effect of Tin-to-Chelate Ratio, Chelate Content and Surface Polymer on Labeling Efficiency and Biodistribution Behavior. Nuclear Medicine and Biology 1994; 21(1):89-96.
23. Bao A D, Goins B, Klipper R, Negrete G, Phillips W T. Direct Tc-99m labeling of pegylated liposomal doxorubicin (Doxil) for pharmacokinetic and non-invasive imaging studies. Journal of Pharmacology and Experimental Therapeutics 2004; 308(2):419-425.
24. Bao A, Goins B, Klipper R, Negrete G, Phillips W T. Re-186-liposome labeling using Re-186-SNS/S complexes: In vitro stability, imaging, and biodistribution in rats. J Nucl Med 2003; 44(12):1992-1999.
25. Marik J, Tartis M S, Zhang H, Fung J Y, Kheirolomoom A, Sutcliffe J L, et al. Long-circulating liposomes radiolabeled with [F-18]fluorodipalmitin ([F-18]FDP). Nuclear Medicine and Biology 2007; 34(2):165-171.
26. Keller B O, Li L. Three-layer matrix/sample preparation method for MALDI MS analysis of low nanomolar protein samples. Journal of the American Society for Mass Spectrometry 2006; 17(6):780-785.
27. Chan W C, White. P D. Fmoc solid phase peptide synthesis: a practical approach. New York: Oxford University Press, 2000.
28. Logan J. Graphical analysis of PET data applied to reversible and irreversible tracers. Nuclear Medicine and Biology 2000; 27(7):661-670.
29. Koning G A, Schiffelers R M, Wauben M H M, Kok R J, Mastrobattista E, Molema G, et al. Targeting of angiogenic endothelial cells at sites of inflammation by dexamethasone phosphate-containing RGD peptide liposomes inhibits experimental arthritis. Arthritis and Rheumatism 2006; 54(4):1198-1208.

30. Moghimi S M, Hamad I, Andresen T L, Jorgensen K, Szebeni J. Methylation of the phosphate oxygen moiety of phospholipid-methoxy(polyethylene glycol) conjugate prevents PEGylated liposome-mediated complement activation and anaphylatoxin production. Faseb Journal 2006; 20(14):2591-2593.

The invention claimed is:

1. A composition for delivering a compound to a cell, comprising:
   at least one peptide comprising a free C-terminus and a linked N-terminus and a plurality of amino acid residues, said peptide comprising a C-terminal arginine residue positioned at said free C-terminus of said peptide, wherein said peptide targets said composition to said cell;
   a particle for carrying said compound, wherein said particle comprises at least one lipid molecule and a brush layer comprising 1,2-distearoyl-sn-glycero-3-phosphoethanolamine-N-[methoxy(polyethylene glycol)-2000] ('DSPE-PEG2000); and
   a linking molecule, wherein said linking molecule links said at least one peptide at said linked N-terminus to said particle.

2. The composition of claim 1, wherein said compound comprises a therapeutic agent or an imaging agent.

3. The composition of claim 1, wherein said compound comprises a radiolabel.

4. The composition of claim 3, wherein said radiolabel comprises [$^{18}$F], $^{18}$F-fluorodipalmitin ([$^{18}$F]FDP), or [$^{64}$Cu].

5. The composition of claim 1, wherein said compound comprises a dye.

6. The composition of claim 1, further comprising said compound.

7. The composition of claim 2, wherein said compound comprises amnioterone or digoxin.

8. The composition of claim 6, wherein said compound comprises [$^{18}$F]FDP.

9. The composition of claim 1, wherein said peptide comprises a plurality of arginine residues at said free C-terminus of said peptide.

10. The composition of claim 1, wherein said peptide comprises two arginine residues at said free C-terminus of said peptide.

11. The composition of claim 1, wherein said peptide comprises an amino acid sequence of PPR.

12. The composition of claim 1, wherein said plurality of amino acid residues does not comprise an amino acid sequence selected from the group consisting of: CRPPR (SEQ ID NO: 1), CARPAR (SEQ ID NO: 4), and CPKRPR (SEQ ID NO: 5) at said free C-terminus of said peptide.

13. The composition of claim 1, wherein said peptide is a dimeric peptide.

14. The composition of claim 13, wherein said dimeric peptide is covalently dimerized.

15. The composition of claim 13, wherein said dimeric peptide is covalently dimerized by a cysteine bond.

16. The composition of claim 1, wherein said peptide comprises a CPPRR amino acid sequence (SEQ ID NO: 2) at said free C-terminus of said peptide.

17. The composition of claim 1, wherein said peptide comprises a CRRRR amino acid sequence (SEQ ID NO: 3) at said free C-terminus of said peptide.

18. The composition of claim 1, wherein said peptide binds a scavenger receptor.

19. The composition of claim 1, wherein said peptide comprises a net positive charge at pH 7.2.

20. The composition of claim 1, wherein said peptide comprises 2-6 mol percent of said composition.

21. The composition of claim 20, wherein said peptide comprises 6 mol percent of said composition.

22. The composition of claim 1, wherein said peptide comprises 5 or more, 6 or more, 7 or more, 8 or more, 9 or more, 10 or more, 50 or more, 500 or more, or 5000 or more amino acid residues.

23. The composition of claim 1, wherein said peptide comprises 5 amino acid residues.

24. The composition of claim 1, wherein said peptide comprises 10 percent, 20 percent, 30 percent, 40 percent, 50 percent, or 80 percent arginine residues.

25. The composition of claim 1, wherein said peptide comprises 40 percent arginine residues.

26. The composition of claim 1, comprising a plurality of peptides.

27. The composition of claim 26, comprising at least 6000 peptides.

28. The composition of claim 27, comprising at least 6000 dimeric peptides.

29. The composition of claim 1, wherein said particle comprises a liposome, a phospholipid based liposome, a microbubble, a nanodroplet, a virus, a caveolae, or a micelle.

30. The composition of claim 1, wherein said particle comprises at least one fatty acid.

31. The composition of claim 1, wherein said lipid comprises 1,2-dipalmitoyl-sn-glycero-3-phosphocholine (DPPC).

32. The composition of claim 1, wherein said particle comprises a phospholipid-based liposome.

33. The composition of claim 32, wherein said phospholipid-based liposome comprises DPPC, a lipid-linker-peptide (LPP), and an ammonium salt of 1,2-distearoyl-sn-glycero-3-phosphoethanolamine-N-[methoxy(polyethylene glycol)-2000] (DSPE-PEG2000).

34. The composition of claim 32, wherein said brush layer is 2000 $M_w$.

35. The composition of claim 1, wherein said linking molecule comprises PEG.

36. The composition of claim 1, wherein said linking molecule is 3600 $M_w$.

37. The composition of claim 1, wherein said cell is a mammalian cell, a human cell, a cardiac cell, an endothelial cell, a cardiac endothelial cell, a HCAEC cell, a HUVEC cell, a brain cell, or a cancer cell.

38. The composition of claim 1, wherein said cell is a cardiac endothelial cell.

39. The composition of claim 1, wherein said composition is used for PET imaging.

40. The composition of claim 1, comprising:
   a plurality of peptides, wherein said peptides comprise a CPPRR amino acid sequence (SEQ ID NO: 2) or a CRRRR amino acid sequence (SEQ ID NO: 3) at the free C-terminus of said peptides and said peptides are dimerized;
   a liposome comprising a PEG brush layer of 2000 $M_w$, wherein said liposome further comprises DPPC and a compound [$^{18}$F]FDP, and wherein said liposome is coated with 6 mol % of said peptides; and
   a linking molecule comprising a PEG spacer of 3600 $M_w$, wherein said linking molecule links said peptides and said liposome.

41. A method for targeting a compound to a cell in a subject, comprising administering said composition of claim 1 to the subject.

* * * * *